United States Patent
Allerton et al.

(10) Patent No.: US 6,919,457 B2
(45) Date of Patent: Jul. 19, 2005

(54) 3-(IMIDAZOLYL)-2-AMINOPROPANOIC ACIDS

(75) Inventors: Charlotte Moira Norfor Allerton, Sandwich (GB); Mark Edward Bunnage, Sandwich (GB); John Steele, Sandwich (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/814,875

(22) Filed: Mar. 31, 2004

(65) Prior Publication Data

US 2004/0192668 A1 Sep. 30, 2004

Related U.S. Application Data

(62) Division of application No. 10/348,883, filed on Jan. 22, 2003, now Pat. No. 6,759,426.
(60) Provisional application No. 60/362,377, filed on Mar. 6, 2002.

(30) Foreign Application Priority Data

Jan. 22, 2002 (GB) .............................................. 0201387
Jan. 28, 2002 (GB) .............................................. 0201911

(51) Int. Cl.$^7$ ........................................... C07D 403/06
(52) U.S. Cl. ....................... 546/210; 546/397; 546/326; 548/314.7
(58) Field of Search ...................... 548/314.7; 546/210, 546/397, 326

(56) References Cited

U.S. PATENT DOCUMENTS 6,759,426 * 7/2004 Allerton et al. .............. 514/397

* cited by examiner

*Primary Examiner*—Laura L. Stockton
(74) *Attorney, Agent, or Firm*—Daniel S. Kasten

(57) ABSTRACT

Compounds according to formula (I) wherein n is 1–4, $R^1$ is optionally substituted $C_{1-6}$ alkyl, $C_{2-6}$ alkenyl, or $C_{2-6}$ alkynyl, Heterocycle, Aromatic heterocycle, Aryl or hydrogen and $R^2$, $R^3$, $R^4$, $R^5$, $R^6$, $R^7$ and $R^8$ are each independently selected from hydrogen and optionally substituted $C_{1-6}$ alkyl are novel. They are useful in the treatment of thrombotic conditions and other pathologies associated with fibrin deposition.

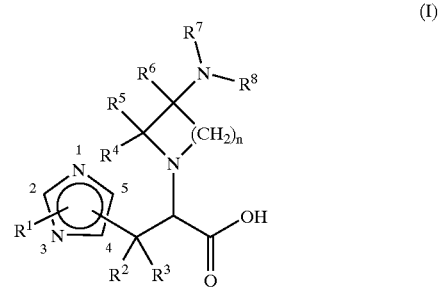

(I)

1 Claim, No Drawings

US 6,919,457 B2

3-(IMIDAZOLYL)-2-AMINOPROPANOIC ACIDS

This application is a divisional application of U.S. application Ser. No. 10/348,883 filed Jan. 22, 2003, now U.S. Pat. No. 6,759,426, which claims priority to UK 0201387.8 filed Jan. 22, 2002; UK 0201911.5 filed Jan. 28, 2002 (37 C.F.R. §1.55(a)), which was filed under the Paris Convention for the Protection of Industrial Property and was filed in the United Kingdom with, and received by The Patent Office, Cardiff Road, Newport, South Wales, NP10 8QQ; and U.S. Provisional Application No. 60/362,377 filed Mar. 6, 2002, now abandoned.

The present invention relates to a series of novel 3-(imidazolyl)-2-(3'-amino-polymethyleneimino)propanoic acid derivatives that are inhibitors of TAFIa inhibitors and are useful in the treatment of disease.

BACKGROUND

Sophisticated mechanisms have evolved in mammals to repair the body in the event of vascular injury and so maintain hemostasis. The injured blood vessel constricts to reduce the blood flow to the area, platelets aggregate to reduce the loss of blood from the area, and fibrinogen is cleaved to produce fibrin which then polymerises and forms a clot. This clot covers the area of vascular damage, preventing blood loss. Polymerised fibrin also provides a provisional matrix which enhances the subsequent repair process. Once the blood vessel has been repaired the clot dissolves. The process leading to the formation of the clot is the coagulation cascade, and the process leading to its dissolution is the fibrinolysis cascade. Imbalances in the blood coagulation process are thought to be at the origin of a large and disparate number of disease conditions, which are linked by an unwanted build up of fibrin. The scale of fibrin build up is determined by the delicate equilibrium between the two biochemical cascades in the human body. Agents that can modulate the balance between coagulation and fibrinolysis are therefore potentially valuable in the treatment of these disease conditions.

Studies have shown that coagulation and fibrinolysis are linked through the generation of α-thrombin. α-Thrombin is the final product of the blood coagulation cascade and is responsible for the conversion of fibrinogen into fibrin. In addition to mediating coagulation, α-thrombin also reduces the rate at which blood clots are broken down by the serine protease plasmin. The protein that mediates this antifibrinolytic effect of α-thrombin is TAFI (Thrombin Activatable Fibrinolysis Inhibitor).

TAFI is a 60 kDa glycoprotein found in human plasma. It is also known as procarboxypeptidase B, carboxypeptidase B, plasma carboxypeptidase B, carboxypeptidase U and carboxypeptidase R. Following initiation of the coagulation cascade it is transformed into an activated form, TAFIa, whereupon it acts upon the fibrin matrix of the developing blood clot to prevent its dissolution. TAFI circulates in normal plasma at a concentration of about 75 nM in an inactive form. Thrombin converts the inactive zymogen to the active TAFI (TAFIa), a reaction that is augmented about 1250-fold by thrombomodulin. Once activated, TAFIa cleaves both C-terminal arginine and lysine residues from the developing fibrin clot. The removal of these dibasic amino acids from the surface of the fibrin matrix attenuates clot lysis by inhibiting the binding of the key mediators of fibrinolysis: tissue plasminogen activator (tPA) and its substrate, plasminogen, which is the precursor of plasmin. Both tPA and plasminogen contain a structural motif called a kringle domain which binds tightly to C-terminal lysine residues. The removal of these binding sites prevents the formation of a ternary complex between tPA, plasminogen and fibrin and this inhibits the conversion of plasminogen to plasmin, thus protecting the clot from rapid degradation.

In the presence of a TAFIa inhibitor, TAFIa will not be able to act upon a developing fibrin clot as described above to inhibit fibrinolysis of the clot. Thus a TAFIa inhibitor should serve to enhance fibrinolysis.

It can be seen that, in pathologies where the normal equilibrium between coagulation and fibrinolysis is disturbed in favour of coagulation, there will be a larger amount of fibrin present than normal. This makes it more likely that the subjects will develop one or more of the conditions in which thrombus build up is implicated. Such subjects can be expected to benefit from treatment with a pro-fibrinolytic agent. McKay et al. (*Biochemistry* 1978, 17, 401) disclose the testing of a number of compounds as competitive inhibitors of bovine carboxypeptidase B of pancreatic origin. Inhibition was measured by the inhibitor's efficiency in protecting the active centre tyrosine and glutamic acid of bovine carboxypeptidase B from irreversible alkylation by bromoacetyl-D-arginine or bromoacetamidobutylguanidine. It is suggested that such inhibitors could act as bradykinin potentiators. Bovine enzymes of pancreatic origin are very different to those found in human plasma, so one would not expect inhibitors of one to inhibit the other. Moreover, such inhibitors are directed towards a very different utility. Accordingly this disclosure provides no teaching of TAFIa inhibitors or their utility.

Redlitz et al. (*J. Clin. Invest.* 1995, 96, 2534) teach the involvement of plasma carboxypeptidase B (pCPB, or TAFI) in the formation of clots. The lysis of blood clots was followed in the absence and presence of pCPB, whereupon it was found that the presence of pCPB slowed clot lysis. To confirm that pCPB was responsible two control reactions were run; one where the lysis experiment was repeated in the presence of pCPB and potato carboxypeptidase inhibitor, PCI, and a second where the lysis reaction was conducted in the presence of plasma from which pCPB was removed. In both cases lysis proceeded uninhibited.

Boffa et al. (*J. Biol. Chem.* 1998, 273, 2127) compare plasma and recombinant TAFI and TAFIa with respect to glycosylation, activation, thermal stability and enzymatic properties. Inhibition constants for three competitive inhibitors were determined: ε-aminocaproic acid (ε-ACA), 2-guanidinoethylmercaptosuccinic acid (GEMSA) and potato carboxypeptidase inhibitor (PCI).

There are large numbers of carboxypeptidases (i.e. enzymes that cleave the C-terminal amino acid from a peptide). They may be classified as acidic, neutral or basic, depending on the type of amino acid they cleave. Basic carboxypeptidases cleave arginine, lysine and histidine. TAFIa is a member of a specific subset of the basic carboxypeptidases. In terms of the present invention, the inhibitors disclosed above by Redlitz et al. and Boffa et al. are too weak, non-specific or otherwise unsuitable to be considered as suitable TAFIa inhibitors for therapeutic application. Further, whilst the role of TAFIa in clot lysis is explained, there is no suggestion that TAFIa inhibitors can be used to treat disease.

U.S. Pat. No. 5,993,815 teaches the use of a peptide that binds to the TAFI zymogen, thereby inhibiting its activation, to treat those disorders where a C-terminal lysine or arginine is cleaved from an intact peptide. Suitable disorders are arthritis, sepsis, thrombosis, strokes, deep vein thrombosis, and myocardial infarctions. The peptide used is an antibody or a functionally active fragment. The peptide should be used in an amount to promote fibrinolysis in vivo.

WO00/66550 and WO00/66557 disclose broad classes of compounds useful as inhibitors of carboxypeptidase U. Inhibitors of carboxypeptidase U are postulated to facilitate fibrinolysis and thus the compounds are taught as useful in the treatment of thrombotic conditions. There is no data to support this assertion, though details of a suitable assay are given.

WO00/66152 discloses formulations containing a carboxypeptidase U inhibitor and a thrombin inhibitor. Suitable carboxypeptidase U inhibitors are those of WO00/66550. The formulations are taught as primarily useful in treating thrombotic conditions.

WO01/19836 discloses a series of phosphonate esters and analogues thereof as carboxypeptidase B inhibitors that are suitable for the treatment or prevention of thrombotic diseases.

WO02/14285 discloses a series of α-imidazolylmethyl-ω-aminocarboxylic acids and $N^\alpha$-(ω-aminoalkyl)-histidine derivatives that are inhibitors of TAFIa. The compounds are considered to be potentially useful in the treatment of a number of conditions.

The present invention discloses a further class of TAFIa inhibitors.

DESCRIPTION OF THE INVENTION

In a first aspect, the present invention provides a compound according to general formula (I)

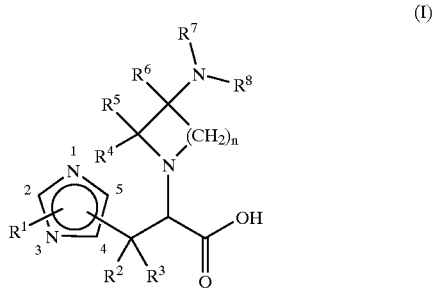

(I)

wherein:

n is 1, 2, 3 or 4;

$R^1$ is selected from a. an optionally substituted straight chain or branched chain $C_{1-6}$ alkyl group, b. an optionally substituted straight chain or branched chain $C_{2-6}$alkenyl group, c. an optionally substituted straight chain or branched chain $C_{2-6}$alkynyl group, d. Aryl, e. Aromatic heterocycle, f. Heterocycle, and g. hydrogen;

where the optional substituents in groups (a), (b) and (c) above are selected from: $C_{3-7}$ cycloalkyl, Aryl, Aromatic heterocycle, Heterocycle, $OR^9$, $NR^9R^{10}$, $S(O)_pR^9$, $OC(O)R^{10}$, $CO_2R^9$, $CONR^9R^{10}$, $SO_2NR^9R^{10}$, halo and $NHSO_2R^9$, and where p is 0, 1 or 2;

$R^2$, $R^3$, $R^4$, $R^5$, $R^6$, $R^7$ and $R^8$ are each independently selected from hydrogen and straight chain or branched chain $C_{1-6}$ alkyl optionally substituted by $OR^9$ or halo;

$R^9$ and $R^{10}$ are each independently selected from hydrogen and straight chain or branched chain $C_{1-6}$ alkyl;

Aryl is a 6–14 membered aromatic monocyclic or fused polycyclic carbocyclic group optionally substituted with one or more groups selected from $R^{11}$, halo, $OR^{12}$, $NR^{12}R^{13}$, $NR^{12}CO_2R^{11}$, $CO_2R^{12}$, $NR^{12}SO_2R^{11}$, CN, haloalkyl, O(haloalkyl), $SR^{12}$, $S(O)R^{11}$, $SO_2R^{11}$, $OC(O)R^{12}$, $SO_2NR^{12}R^{13}$ and $C(O)NR^{12}R^{13}$, where $R^{11}$ is straight chain or branched chain $C_{1-6}$ alkyl and $R^{12}$ and $R^{13}$ are each independently selected from hydrogen and straight chain or branched chain $C_{1-6}$ alkyl;

Aromatic heterocycle is a 5 to 7 membered aromatic ring containing from 1 to 3 heteroatoms, each independently selected from O, S and N, said ring being optionally substituted with one or more groups selected from $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{12}$, $NR^{12}R^{13}$, $CO_2R^{12}$, $NR^{12}CO_2R^{13}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$, or a tautomer thereof, or a pharmaceutically acceptable salt or solvate of said compound or said tautomer.

As used herein:

i. Halo includes fluoro, chloro, bromo and iodo groups.

ii. Haloalkyl includes monohaloalkyl, polyhaloalkyl and perhaloalkyl, such as 2-bromoethyl, 2,2,2-trifluoroethyl, chlorodifluoromethyl and trichloromethyl.

iii. Unless otherwise indicated, alkyl includes straight chain and branched chain alkyl.

It will be understood that, in the compounds according to general formula (I), the $R^1$ group and $C(R^2)(R^3)$(amino acid) group may be attached at any atom of the imidazole ring that is available to form a covalent bond, and that it is not intended that the general formula should be interpreted as limiting the $R^1$ group to the $C^2$- and $N^3$-positions, nor the $C(R^2)(R^3)$(amino acid) group to the $C^4$- and $C^5$-positions. It will further be understood that the two groups cannot both be attached to the same atom of the imidazole ring, and that only one of the nitrogen atoms (by convention designated $N^1$) of the imidazole ring is available to form a covalent bond. Thus the possible substitution patterns are 1,2-; 1,4-; 1,5-; 2,4- and 2,5-. When the imidazole is 2,4- or 2,5- substituted then there is a hydrogen atom attached at the $N^1$-position.

Certain compounds according to formula (I) may exist in more than one tautomeric form. If the imidazole of general formula (I) is substituted at the 2- and 4-positions the 2,4-disubstituted imidazole can tautomerise to form the corresponding 2,5-disubstituted imidazole. Furthermore, where a compound includes an Aromatic heterocyle that is substituted with a hydroxyl group it may exist as the 'keto' tautomer. The tautomeric relationship between 2-hydroxypyridine and 2-pyridone is a well known example of this phenomenon. All such tautomers of compounds of formula (I), including mixtures thereof, are included in the scope of the present invention.

The compounds of formula (I) contain one or more asymmetric carbon atoms (chiral centers) and can therefore exist in two or more optical stereoisomeric forms such as enantiomers, diastereomers and epimers. Where the compounds of formula (I) contain a carbon-carbon double bond, cis (Z)/trans (E) stereoisomerism may also occur. All such individual stereoisomers of the compounds of formula (I) and mixtures thereof, including racemates, are included in the scope of the present invention.

Individual stereoisomers may be separated from mixtures by conventional techniques such as, for example, by fractional crystallization or by chromatography of the mixture of compounds or of a suitable salt or derivative thereof. In particular, individual enantiomers of the compounds of formula (I) may be prepared by resolution, such as by H.P.L.C. of the corresponding racemate using a suitable chiral support or by fractional crystallisation of the diastereoisomeric salts formed by reaction of the corresponding racemate with a suitable optically active acid or base, as appropriate. The individual enantiomers may also be obtained from a corresponding optically pure intermediate prepared by such a resolution method. These general principles are discussed in more detail by J. Jacques and A. Collet ("Enantiomers, Racemates and Resolutions", Wiley, N.Y., 1981) and by W. Liu ("Handbook of Chiral Chemicals", D. Ager (ed.), M. Dekker, N.Y., 1999; chapter 8).

It will be appreciated that the compounds of formula (I) have both acidic and basic functional groups. Therefore, in addition to the uncharged form depicted in the general formula, they may exist as internal salts (zwitterions). Furthermore, they may form pharmaceutically acceptable salts with acids and bases. Such zwitterions and salts are included within the scope of the invention.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent. Salts may also be prepared by ion exchange, such as by equilibrating a solution of a compound of formula (I) with an appropriate ion exchange resin. Ion exchange may also be used to convert one salt form of a compound of formula (I), such as a salt with an acid or base that is not pharmaceutically acceptable, to another salt form. These methods are generally well known in the art. Suitable acid addition salts are formed from acids which form non-toxic salts and examples are the hydrochloride, hydrobromide, hydroiodide, sulfate, bisulfate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts. For a review of pharmaceutically acceptable salts see Berge et al. (*J. Pharm. Sci.*, 1977, 66, 1).

The compounds of formula (I) may form pharmaceutically acceptable solvates (including hydrates). These solvates are also included in the scope of the present invention.

The compounds of formula (I) may exist in one or more crystalline forms. These polymorphs, including mixtures thereof are also included within the scope of the present invention.

The scope of the present invention further includes prodrugs of compounds of formula (I), i.e. pharmaceutically acceptable derivatives of the compounds in which one or more of the functional groups explicitly recited above have been modified such that they are converted to the parent compounds in vivo. Suitable prodrugs are discussed in *Drugs of Today* 1983, 19, 499–538 and *Annual Reports in Medicinal Chemistry* 1975, 10, 306–326.

The absolute stereochemistry of the compounds of formula (I) may be as depicted in formula (IA) or formula (IB) below. By convention the absolute stereochemistry at the chiral center of (IA) is designated as 'S' and that of (IB) is 'R'. The compounds of formula (IA) are particularly preferred.

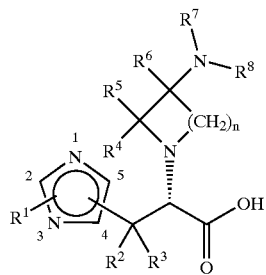

(IA)

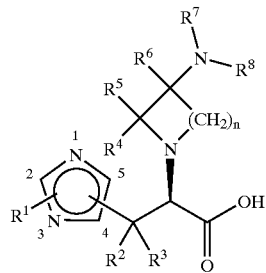

(IB)

Preferred compounds of formula (I) include those where the imidazole is substituted at the $C^2$ or $C^4$ positions by the $C(R^2)(R^3)$(amino acid) group to give compounds of formulae (IC) and (ID) respectively. Particularly preferred are those compounds of formula (I); where $R^1$ is attached at the $C^4$ position of the imidazole moiety and the $C(R^2)(R^3)$ (amino acid) group is attached at the $C^2$ position so as to give the 2,4-disubstituted imidazole of formula (IC$^1$) or where $R^1$ is attached at the $N^1$ position of the imidazole moiety and the $C(R^2)(R^3)$(amino acid) group is attached at the $C^4$ position so as to give the 1,4-disubstituted imidazole of formula (ID$^1$). Most preferred are those compounds of formula (I) where $R^1$ is attached at the $N^1$ position of the imidazole moiety and the $C(R^2)(R^3)$(amino acid) group is attached at the $C^4$ position so as to give the 1,4-disubstituted imidazole of formula (ID$^1$).

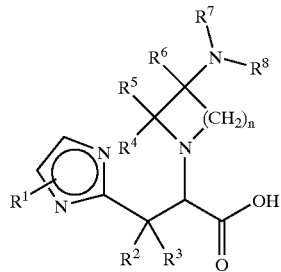

(IC)

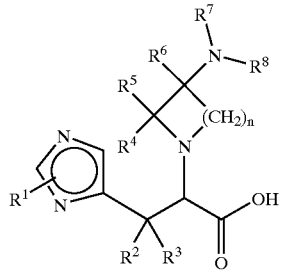

(ID)

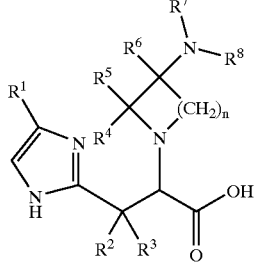

(IC¹)

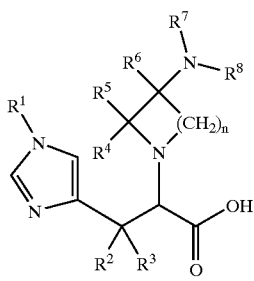

(ID¹)

Preferably n is 2 or 3. More preferably n is 2.

Preferably $R^1$ is hydrogen, Aryl or a $C_{1-6}$ alkyl group optionally substituted by a group selected from a $C_{3-7}$ cycloalkyl group and Aryl. More preferably $R^1$ is hydrogen, Aryl or a $C_{1-6}$ alkyl group optionally substituted by a group selected from cyclohexyl and Aryl. In one still more preferred embodiment $R^1$ is phenyl, $C_{1-5}$ alkyl, phenyl-$C_{1-3}$ alkyl, cyclohexyl-$C_{1-3}$ alkyl or hydrogen. In a second still more preferred embodiment $R^1$ is Aryl, propyl or hydrogen. Most preferably $R^1$ is propyl.

Preferably $R^2$, $R^3$, $R^4$, $R^5$, $R^6$, $R^7$ and $R^8$ are each independently selected from hydrogen and $C_{1-3}$ alkyl. More preferably $R^2$, $R^3$, $R^4$, $R^5$, $R^6$, $R^7$ and $R^8$ are each independently selected from hydrogen and methyl. Most preferably $R^2$, $R^3$, $R^4$, $R^5$, $R^6$, $R^7$ and $R^8$ are all hydrogen.

Preferably $R^9$ and $R^{10}$ are each independently selected from hydrogen and $C_{1-3}$ alkyl. More preferably $R^9$ and $R^{10}$ are each independently selected from hydrogen and methyl. Most preferably $R^9$ and $R^{10}$ are both hydrogen.

Aryl includes optionally substituted phenyl, naphthyl, anthracenyl and phenanthrenyl. Preferably Aryl is phenyl optionally substituted by 1–3 groups selected from $R^{11}$, halo, $OR^{12}$, $NR^{12}R^{13}$, $CO_2R^{12}$, $NHSO_2R^{11}$, CN and haloalkyl. More preferably Aryl is phenyl.

Preferably Aromatic heterocycle is a 5 or 6 membered aromatic ring containing from 1 to 3 heteroatoms each independently selected from O, S and N, including furyl, thienyl, pyrrolyl, oxazolyl, isoxazolyl, thiazolyl, isothiazolyl, imidazolyl, oxadiazolyl, thiadiazolyl, triazolyl, pyridyl, pyridazinyl, pyrimidinyl, pyrazinyl and triazinyl, optionally substituted by 1–3 groups selected from $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$. More preferably Aromatic heterocycle is defined as a 5 or 6 membered aromatic ring containing 1 or 2 heteroatoms, each independently selected from O, S and N, said heterocycle group optionally substituted by 1–3 groups selected from $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$. Most preferably Aromatic heterocycle is an unsubstituted 5 or 6 membered aromatic ring containing 1 or 2 heteroatoms, each independently selected from O, S and N.

Preferably, Heterocycle is a 3 to 8 membered ring containing 1 or 2 heteroatoms, each independently selected from O, S and N, said ring being saturated or partially saturated, optionally substituted by 1 to 3 groups selected from $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$. More preferably, Heterocycle is a 5 or 6 membered ring containing 1 or 2 heteroatoms, each independently selected from O, S and N, said ring being saturated or partially saturated, optionally substituted by 1 to 3 groups selected from: $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}$ $R^{13}$ and $C(O)NR^{12}R^{13}$. Most preferably, Heterocycle is an unsubstituted 5 or 6 membered ring containing 1 or 2 heteroatoms, each independently selected from O, S and N, said ring being saturated or partially saturated, including oxiranyl, azetidinyl, tetrahydrofuranyl, thiolanyl, pyrrolidinyl, dioxolanyl, dihydropyranyl, tetrahydropyranyl, morpholinyl, piperidinyl and piperazinyl.

Preferred compounds of the present invention are:
(+)-(2S)-2-[(3S)-3-aminopyrrolidinyl]-3-(1H-imidazol-4-yl)propanoic acid (Example 2);
(+)-(2S)-2-[(3S)-3-aminopyrrolidinyl]-3-(1-propyl-1H-imidazol-4-yl)propanoic acid (Example 4);
(2S)-2-[(3S)-3-aminopyrrolidinyl]-3-(1-isopentyl-1H-imidazol-4-yl)propanoic acid (Example 5);
(+)-(2S)-2-[(3S)-3-aminopyrrolidinyl]-3-[1-(2-cyclohexylethyl)-1H-imidazol-4-yl]propanoic acid (Example 6);
(+)-(2S)-2-[(3S)-3-aminopyrrolidinyl]-3-[1-(2-phenylethyl)-1H-imidazol-4-yl]propanoic acid (Example 8); and
(+)-(2S)-2-[(3S)-3-aminopyrrolidinyl]-3-[1-phenyl-1H-imidazol-4-yl]propanoic acid (Example 9).

Particularly preferred is (+)-(2S)-2-[(3S)-3-aminopyrrolidinyl]-3-(1-propyl-1H-imidazol-4-yl)propanoic acid (Example 4).

The compounds of formula (I) are inhibitors of TAFIa. Inhibition of TAFIa can be demonstrated using an assay based on the method of Boffa et al. (*J. Biol. Chem.* 1998, 273, 2127) as further described below. The activity of the compounds is characterized by a calculated $K_i$ value. Generally the compounds of the present invention have a $K_i$ value of 10 $\mu$M or less. Better compounds have a k; value of 1 $\mu$M or less, or even 100 nM or less. The most potent compounds have a $K_i$ value of 25 nM or less.

The compounds of formula (I) are selective for TAFIa over other carboxypeptidases, and particularly carboxypeptidase N (CPN). Unwanted inhibition of CPN is considered to be the most likely cause of undesirable side effects in clinical use. Selectivity can be expressed as the ratio of the $K_i$ for TAFIa to the $K_i$ for CPN. Generally the compounds of the present invention have a selectivity ratio of at least 5. Better compounds have a selectivity ratio of at least 10. The most selective compounds have a selectivity ratio of at least 50.

The compounds of formula (I) may be prepared according to the general methods which are described below and in the Examples and Preparations section. These methods provide a further aspect of the present invention. Nevertheless, the skilled man will appreciate that the compounds of the invention could be made by methods other than those herein described, by adaptation of the methods herein described and/or adaptation of a plethora of methods known in the art. It is to be understood that the synthetic transformation methods specifically mentioned herein may be carried out in various different sequences in order that the desired substances can be efficiently assembled. The skilled chemist will exercise his judgement and skill as to the most efficient sequence of reactions for the synthesis of a given target substance.

It will be apparent to those skilled in the art that sensitive functional groups may need to be protected and deprotected during the synthesis of a substance of the invention. This may be achieved by conventional techniques, for example as described by T. W. Greene and P. G. M. Wuts ("Protective Groups in Organic Synthesis", $3^{RD}$ edition, Wiley-Interscience, N.Y., 1999).

Compounds of formula (I) may be prepared from the corresponding esters of formula (II) (wherein $P^1$ is a lower alkyl group, a benzyl group or any other carboxyl protecting group).

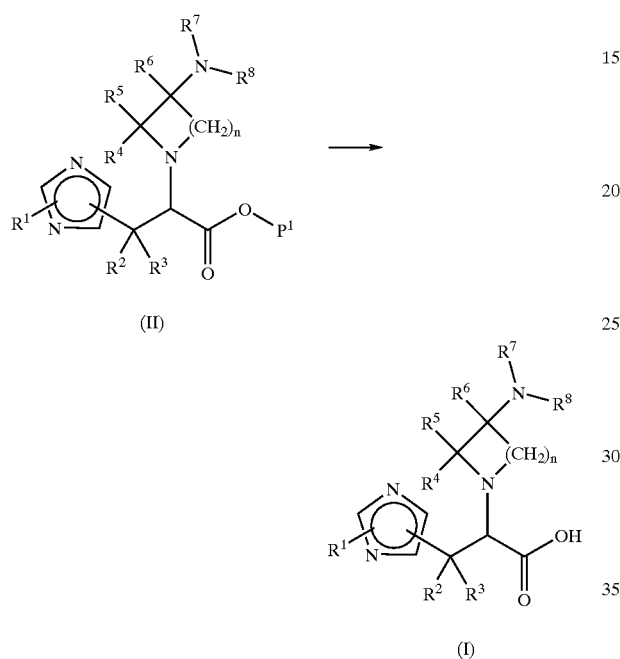

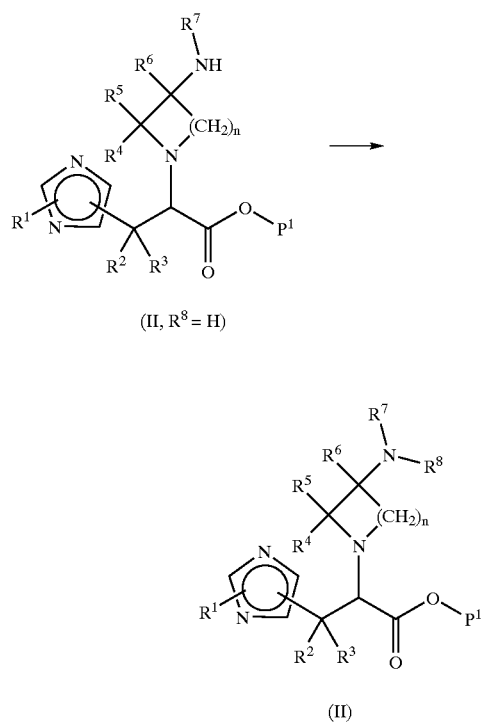

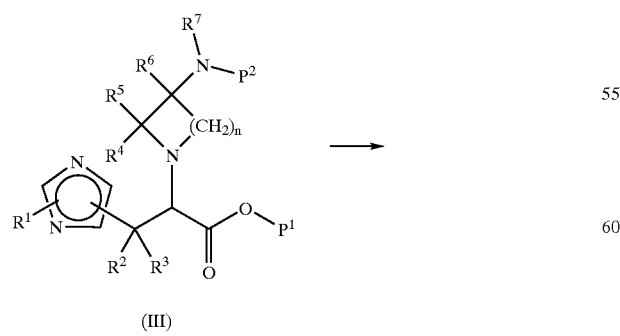

$P^1$ is preferably a lower alkyl group such as methyl or ethyl, in which case suitable conditions for this step include treatment with NaOH in dioxan for 1–3 days.

Compounds of formula (II) may be prepared from the corresponding protected amines of formula (III) (wherein $P^2$ is a tert-butyloxycarbonyl, benzyloxycarbonyl or fluorenylmethyloxycarbonyl group, or any other amine protecting group). Where $R^8$ is H then the preparation involves only a deprotection step. Where $R^8$ is other than H then a further step is necessary to introduce $R^8$, such as a reductive amination reaction.

Alternatively, compounds of formula (III) may be converted to the corresponding acids (IV) prior to deprotecting the amine to give the compounds of formula (I).

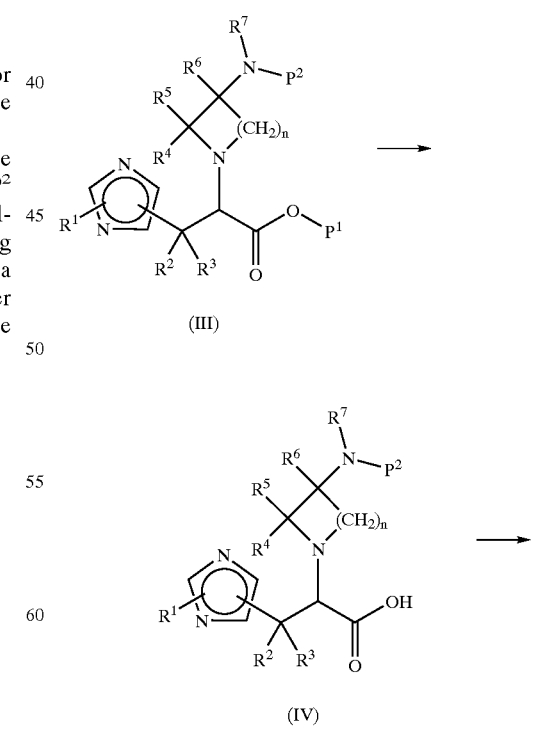

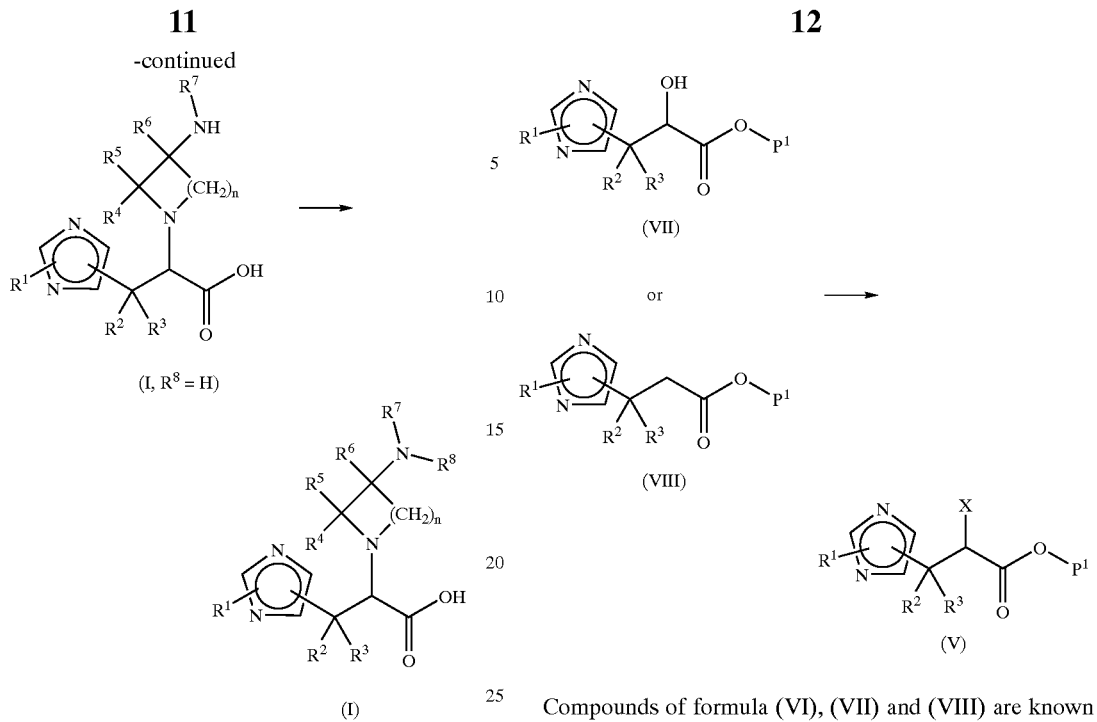

(I, R⁸ = H)

(I)

Compounds of formula (III) may be prepared from imidazoleacetic acid derivatives of formula (V), wherein X is a leaving group such as a chlorine, bromine or iodine atom, or a methanesulphonate or trifluoromethanesulphonate group, by reaction with a cyclic amine of formula (VI).

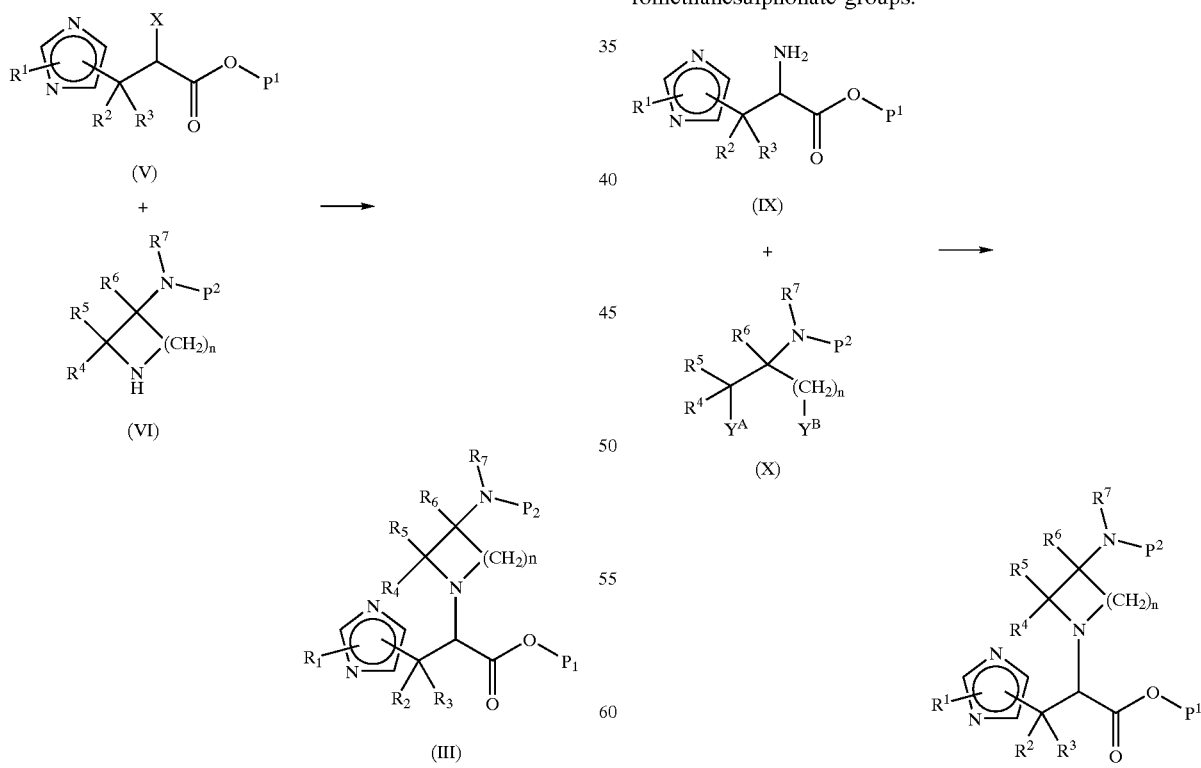

Compounds of formula (V) may be prepared from the corresponding hydroxyacid derivatives of formula (VII) or, where X is Br, by direct halogenation of the esters of formula (VIII).

Compounds of formula (VI), (VII) and (VIII) are known or may be prepared by methods analogous to those used for the preparation of such known compounds.

Compounds of formula (III) may alternatively be prepared from α-aminoimidazoleacetic acid derivatives of formula (IX) by reaction with a compound of formula (X) wherein $Y^A$ and $Y^B$ are leaving groups such as chlorine, bromine or iodine atoms, or methanesulphonate or trifluoromethanesulphonate groups.

Compounds of formula (IX) are known or may be prepared by methods analogous to those used for the preparation of such known compounds. When $Y^A$ and $Y^B$ are the same, compounds of formula (X) may be prepared from the corresponding diol of formula (XI). Compounds of formula (X) where $Y^A$ and $Y^B$ are different may be prepared in a stepwise manner by the elaboration of a suitable difunctional starting material.

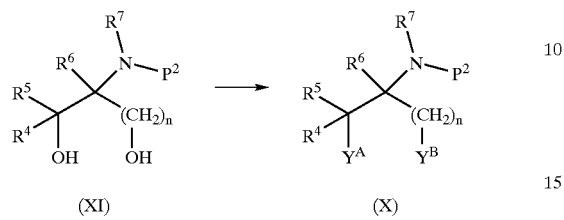

(XI)  (X)

Compounds of formula (XI) may be prepared from the corresponding diesters of formula (XII) or the hydroxyesters of formula (XIII). These compounds, which are derivatives and/or homologues of aminoacids such as aspartic acid, glutamic acid and serine, are generally known or available by simple modification of known methods.

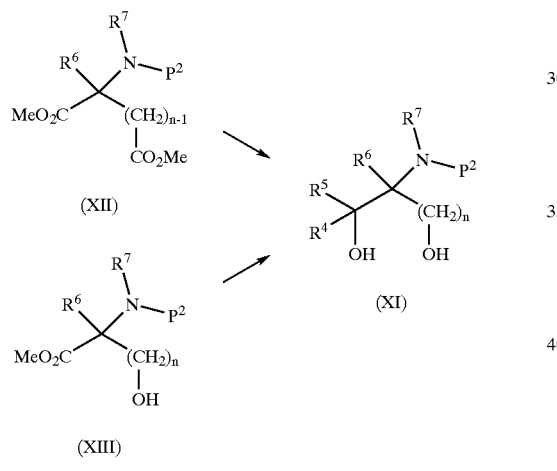

(XII)

(XIII)

(XI)

Suitable conditions for this step include treatment with 2 eq $NaBH_4$ in tetrahydrofuran and methanol.

In a variation of the foregoing, compounds of formula (III) may be prepared by an intramolecular cyclisation of amino-alcohol derivatives of formula (XIV).

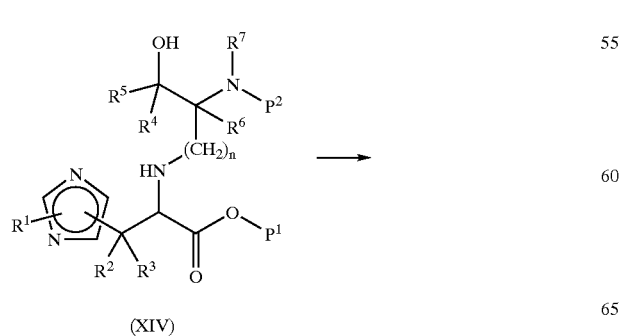

(XIV)

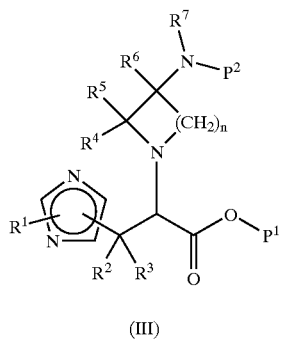

(III)

Suitable conditions for this step include treatment with 1 eq of methanesulfonyl chloride and 2 eq of triethylamine in dichloromethane.

Compounds of formula (XIV) may be prepared by deprotection of a compound of formula (XV) wherein $P^3$ is a benzyl, 2-tetrahydropyranyl or other alcohol protecting group. When $R^7$ is H the hydroxy protecting group may conveniently be protected as an oxazolidine of formula (XVI).

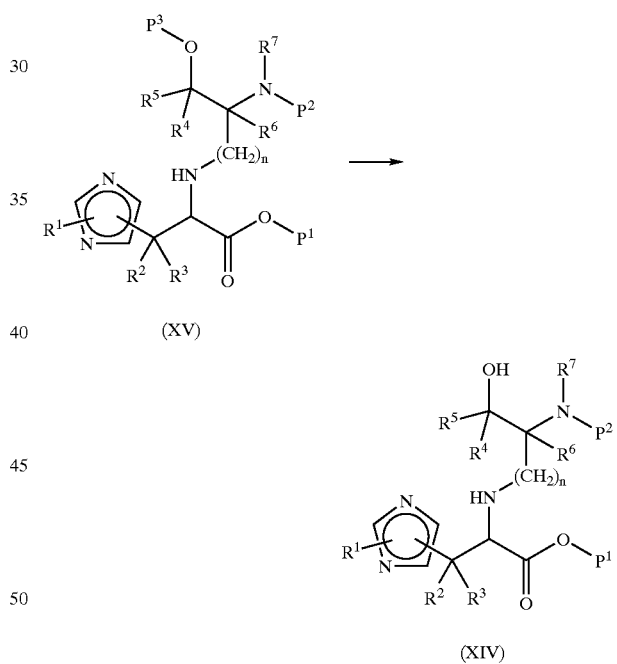

(XV)

(XIV)

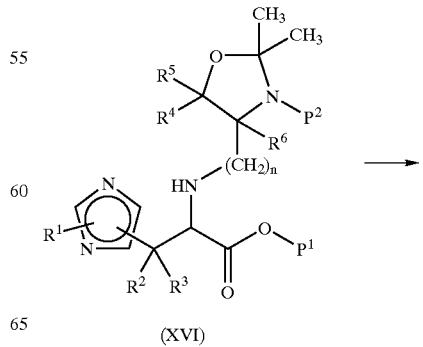

(XVI)

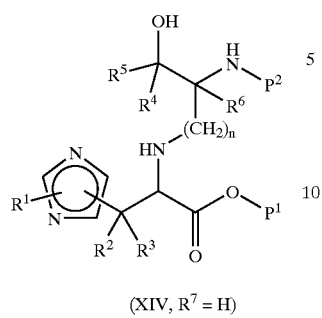

(XIV, R⁷ = H)

The oxazolidine protecting group can be removed by acidic hydrolysis. Suitable conditions for this step include treatment with HCl in dioxan.

Compounds of formula (XV) and (XVI) may be prepared from α-aminoimidazoleacetic acid derivatives of formula (IX) by reaction with aldehydes of formula (XVII) or (XVIII) under reducing conditions.

Suitable conditions for this step include treatment with 4 eq sodium acetate, 3 Å mol sieves and 1–4 eq of sodium triacetoxyborohydride in THF and/or methanol.

Compounds of formula (XVII) and (XVIII) may be prepared by oxidation of alcohols of formula (XIX) and (XX).

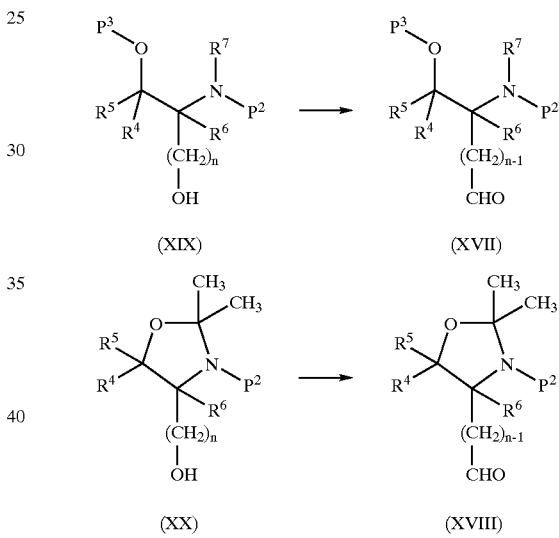

The use of pyridinium chlorochromate in dichloromethane is particularly favoured for this step.

Compounds of formula (XIX) may be prepared via intermediates (XXI) and (XXII) from serine homologues of formula (XXIII), wherein P⁴ is a hydroxyl protecting group that is orthogonal to P³.

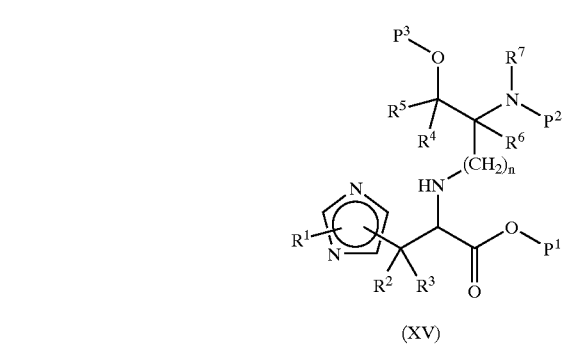

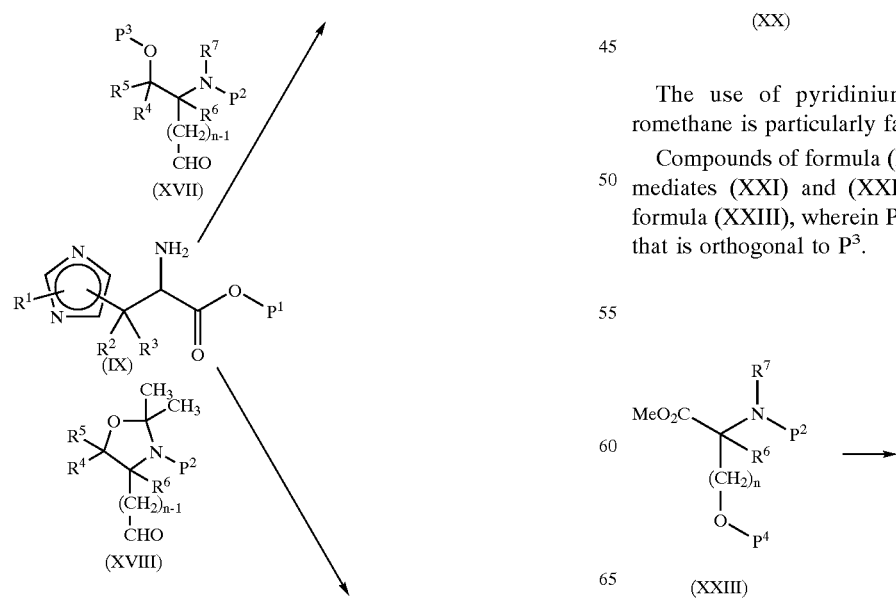

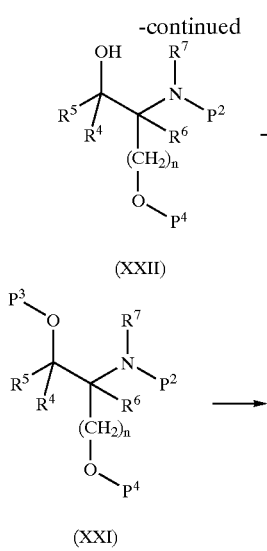

Compounds of formula (XXIII) are generally known.
Compounds of formula (XX) may be prepared from diols of formula (IX) wherein $R^7$ is H.

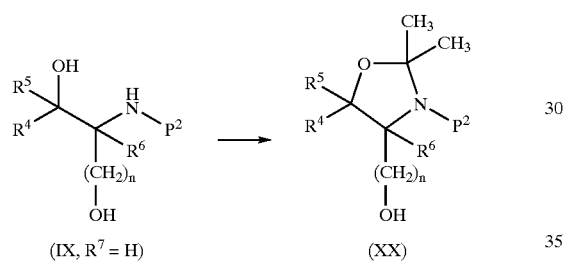

Suitable conditions for this step include treatment with $(MeO)_2CMe_2$ and toluenesulfonic acid.

When $R^1$ is H it may be necessary or convenient to protect the imidazole as its trityl derivative. Accordingly, when $R^1$ is H, compounds of formula (XXIV), (XXV) or (XXVI) may be elaborated by the foregoing methods to provide compounds of formula (XXVII) which, upon deprotection, give compounds of formula (III).

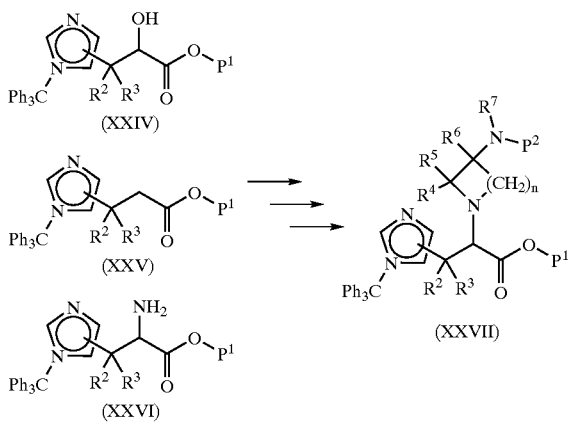

This route may also be useful for the preparation of certain compounds according to formula (I) wherein $R^1$ is attached at the $N^1$ position of the imidazole ring. Compounds of formula (III) wherein $R^1$ is H may be alkylated or arylated to give compounds of formula (III) wherein $R^1$ is other than H and is attached at the $N^1$ position.

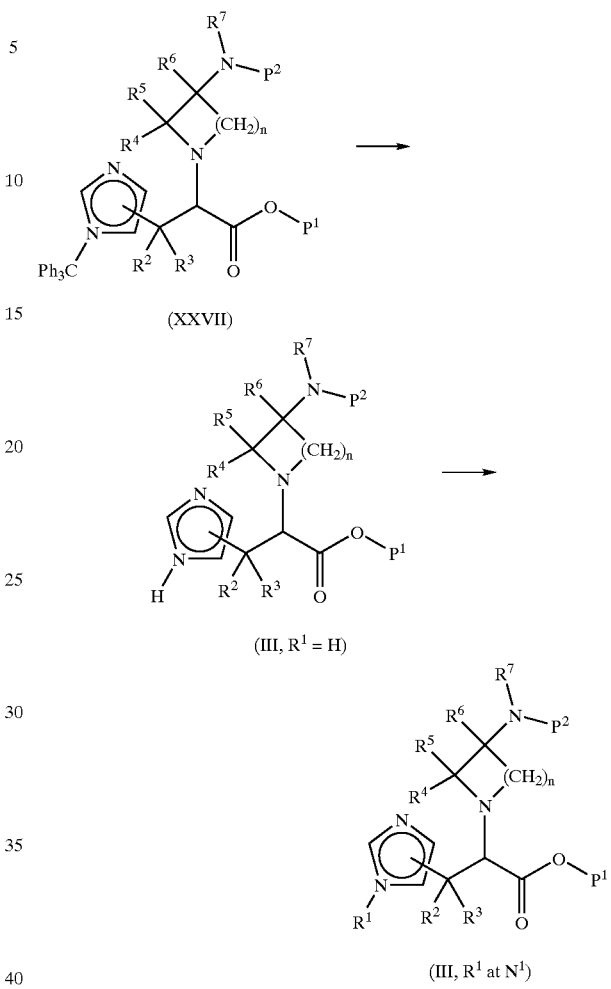

When $R^1$ is an alkyl, alkenyl or alkynyl group it may be introduced in an alkylation reaction. Suitable conditions for this step include treatment with 1.1 eq of cesium carbonate and 1.1 eq of an alkylating agent in N,N-dimethylformamide, or with sodium hydride and 1.1 eq of an alkylating agent in THF. Suitable alkylating reagents include $R^1$—Cl, $R^1$—Br, $R^1$—I, $R^1$—$OSO_2CH_3$ and $R^1$—$OSO_2CF_3$. When $R^1$ is Aryl or Aromatic heterocycle it may be introduced in an arylation reaction. Suitable conditions for this step include treatment with 2 eq of Aryl-B$(OH)_2$ or Aromatic heterocycle-B$(OH)_2$ in the presence of 1.5 eq of copper acetate, 2 eq of pyridine, air and 4 Å molecular sieves.

For the compounds of formula (I) wherein the imidazole is 2,4- or 2,5-disubstituted, it may also be convenient or necessary to use a protecting group at the $N^1$ position.

The compounds of formula (I) are useful as therapeutic agents. The compounds will generally be formulated so as to be amenable to administration to the subject by the chosen route. In a further aspect, therefore, the present invention provides for a pharmaceutical composition comprising a compound of formula (I) or a stereoisomer, tautomer or pharmaceutically acceptable salt, solvate or prodrug thereof and a pharmaceutically acceptable excipient, diluent or carrier selected with regard to the intended route of administration and standard pharmaceutical practice. For example, the compounds of formula (I) can be administered orally, buccally or sublingually in the form of tablets, capsules, ovules, elixirs, solutions or suspensions. These formulations may contain flavouring or colouring agents, and may be adapted for immediate-, delayed-, modified-, sustained-, pulsed- or controlled-release applications.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose and derivatives thereof, milk sugar and high molecular weight polyethylene glycols.

For solutions, suspensions and elixirs, the compounds of the formula (I) may be combined with various sweetening or flavouring agents, colouring matter or dyes, with emulsifying and/or suspending agents, and with diluents such as water, ethanol, propylene glycol and glycerin, and combinations thereof.

The compounds of formula (I) may also be administered in the form of a solution- or suspension-filled soft or hard gelatin capsule. Such capsules are generally made of gelatin, glycerin, water and sorbitol. Hard capsules are distinguished from soft capsules by containing less water and thus having a correspondingly stronger shell. Additional excipients suitable for use in such capsules include propylene glycol, ethanol, water, glycerol and edible oils.

The compounds of formula (I) can also be administered parenterally, for example, intravenously, intra-arterially, intraperitoneally, intrathecally, intraventricularly, intraurethrally, intrasternally, intracranially, intramuscularly or subcutaneously. Such administration may be as a single bolus injection or as a short- or long-duration infusion. For such parenteral administration the compounds are preferably formulated as a sterile solution in water or another suitable solvent or mixture of solvents. The solution may contain other substances such as: salts, particularly sodium chloride, and sugars, particularly glucose or mannitol, to make the solution isotonic with blood; buffering agents such as acetic, citric and phosphoric acids and their sodium salts, such that the pH of the solution is preferably between 3 and 9; and preservatives. The preparation of suitable parenteral formulations under sterile conditions is readily accomplished by standard pharmaceutical techniques well known to those skilled in the art.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant such as dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Alternatively, the compounds of formula (I) can be administered by the vaginal or rectal routes in the form of a suppository or pessary, or the compounds of formula (I) may also be administered dermally or transdermally, for example, by the use of a skin patch.

Alternatively, the compounds of formula (I) can be applied topically in the form of a gel, hydrogel, lotion, solution, cream, ointment or dusting powder. Suitable ointments may contain the active compound suspended or dissolved in, for example, a mixture with one or more of the following: mineral oil, liquid petrolatum, white petrolatum, propylene glycol, polyoxyethylene polyoxypropylene compound, emulsifying wax and water. Suitable lotions or creams may contain the active compound suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Alternatively, the compounds of formula (I) may be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The compounds of formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

Because the compounds of formula (I) are inhibitors of TAFIa they are useful as therapeutic agents in pathologies in which inhibition of TAFIa is beneficial. In a further aspect, therefore, the present invention provides for a compound of formula (I) or a stereoisomer, tautomer, solvate, pharmaceutically acceptable salt or prodrug thereof for use as a medicament. In particular, the present invention provides for the use of a compound of formula (I) or a stereoisomer, tautomer, solvate, pharmaceutically acceptable salt or prodrug thereof in the preparation of a medicament for the treatment or prevention of a condition selected from thrombotic conditions, atherosclerosis, adhesions, dermal scarring, cancer, fibrotic conditions, inflammatory diseases and those conditions which benefit from maintaining or enhancing bradykinin levels in the body. The utility of TAFIa inhibitors for the treatment of thrombotic conditions derives from their potential to promote fibrinolysis while not interfering with coagulation. In most clinically relevant situations thrombus formation is sub-acute, i.e. the thrombus forms slowly. Conventional anti-thrombotic agents block the coagulation pathway and so prevent thrombus growth, but as an unavoidable consequence they also block the clotting response to vascular damage, which results in an increased incidence of hemorrhaging. By promoting fibrinolysis, TAFIa inhibitors accelerate the dissolution of the developing thrombus without interfering with the clotting response. Accordingly, one preferred embodiment of the present invention provides for the use of a compound of formula (I) or a pharmaceutically acceptable salt, solvate or prodrug thereof in the preparation of a medicament for the treatment of a thrombotic condition selected from myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events following surgical revascularisation or intervention, or for improving the outcome of organ transplantation by reducing blood clotting and so preserving organ function. Cardiovascular events following intervention surgery include conditions such as restenosis or reocclusion following interventions such as percutaneous transluminal coronary angioplasty, grafting, stent in-placement, coronary bypass surgery or any other forms of surgical revascularisation or intervention. Disseminated intravascular coagulation includes all conditions resulting from intravascular activation of the coagulation process. This might occur acutely through the release of procoagulant substances (eg. obstetric emergencies, snakebite, crush injury malignancy), by abnormal contact of the blood (eg. infections, burns, extracorporeal circulation, grafts) or though generation of procoagulants in the blood (transfusion reactions, leukemia); or chronically, (eg. toxemia, malignant hypertension, severe liver cirrhosis). Deep vein thrombosis also encompasses what is known as 'economy class syndrome', where clots form in subjects forced to endure cramped conditions for a period of time, such as those sitting in the economy class seats of an aeroplane.

A role for thrombus formation in the pathophysiology of atherosclerosis has recently been highlighted by several independent groups. Non-occlusive thrombi not only restrict blood flow leading to myocardial ischemia and angina pectoris but also, due to incomplete endogenous lysis, may be incorporated into the arterial wall as solidified plaque material enhancing the atherosclerotic process. Long-term administration of a TAFIa inhibitor promotes the lysis of developing thrombi and therefore provides a safe and efficacious treatment which alleviates the symptoms of angina pectoris while impairing the progression of the underlying disease. Conventional treatment of myocardial ischaemia in clinically stable coronary artery disease is predominately designed to reduce cardiac workload and enhance blood flow. Such approaches clearly reduce myocardial ischaemia thus increasing quality of life. However, these strategies have little effect on the pathogenesis of coronary atherosclerosis which is a chronic process of continuous remodeling of the vascular tree in response to varying degrees of vascular injury. Accordingly, another preferred embodiment of the present invention provides for the use of compounds of formula (I) and pharmaceutically acceptable salts, solvates and prodrugs thereof in the preparation of a medicament for the treatment or prevention of atherosclerosis, including atherosclerosis as a consequence of peripheral vascular disease, insulin resistance and Syndrome X, and further including myocardial ischaemia and angina pectoris resulting from atherosclerosis. Atherosclerosis is taken to include both primary and secondary coronary artery disease, in which atherosclerosis restricts the blood supply to the heart. Primary prevention of coronary artery disease means preventing the onset of ischemic complications such as myocardial infarction in patients with no history of coronary artery disease but who have one or more risk factors. Secondary prevention of coronary artery disease means preventing ischemic complications in patients with established coronary artery disease, such as patients who have had a previous myocardial infarction. Syndrome X is a term often used to group together a number of interrelated diseases. The first stage of syndrome X consists of insulin resistance, abnormal cholesterol and triglyceride levels, obesity and hypertension. Any one of these conditions may be used to diagnose the start of Syndrome X. The disease may then progress with one condition leading to the development of another in the group. For example insulin resistance is associated with high lipid levels, hypertension and obesity. The disease then cascades, with the development of each additional condition increasing the risk of developing more serious diseases. This can progress to the development of diabetes, kidney disease and heart disease. These diseases may lead to stroke, myocardial infarction and organ failure. Atherosclerosis is common in patients with Syndrome X.

TAFIa inhibitors are also effective in preventing the formation of adhesions in the body. Most surgical procedures and physical traumas result in bleeding into the cavities between tissues. The blood which collects at these sites then clots forming fibrin-rich thrombi. These thrombi bridge the gaps between adjacent tissues and act as foci for the accumulation of inflammatory cells and fibroblasts. Invading fibroblasts lay down a collagen-rich extracellular matrix which strengthens the adhesion of the tissues producing a firm bond which may then restrict movement. Adhesions have been characterised according to their location and may result following any surgery, e.g. abdominal, orthopaedic, neurological, cardiovascular and ocular surgery. This inappropriate adhesion of tissues post-surgery or trauma is a major issue which can lead to various outcomes, e.g. "aches and pains", "twinges", local inflammation, restriction in mobility, pain, intestinal obstruction and sometimes, in the most severe cases, death. In the case of gynaecological surgery, infertility may result. Additionally clots forming fibrin-rich thrombi are implicated in dermal scarring and restenosis. Without being bound by any theory, it is believed that adhesion formation may be enhanced when a deficiency in fibrinolysis results in enhanced and maintained clot formation. Treatment with a TAFIa inhibitor around and/or after surgical intervention may enhance fibrinolysis of the fibrin-rich thrombi and hence inhibit thrombus formation, accretion and stabilization, thereby inhibiting adhesion formation. A TAFIa inhibitor given either locally as a topical application or systemically may be seen to be of benefit in a range of surgical procedures. In addition, administration of a TAFIa inhibitor may be used to treat adhesions resulting from other forms of non-surgical physical trauma where this has caused internal bleeding. Examples of such trauma might include sporting injuries or anything else resulting in a tear, cut, bruise or induration of the body. Accordingly, another preferred embodiment of the present invention provides for the use of compounds of formula (I) and pharmaceutically acceptable salts, solvates and prodrugs thereof in the preparation of a medicament for the treatment or prevention of a medicament for the treatment or prevention of adhesions or dermal scarring.

TAFIa inhibitors are also effective in inhibiting tumour maturation, progression and metastasis. Without being bound by any theory, it is believed that the hemostatic system is involved at several levels of cancer pathology, including neovascularisation, shedding of cells from the primary tumour, invasion of the blood supply, adherence to the vessel wall and growth at the metastatic site. It is thought that the efficacy of TAFIa inhibitors stems from an ability to reduce fibrin deposition around solid tumours and thereby inhibit the above processes. Accordingly, another preferred embodiment of the present invention provides for the use of compounds of formula (I) and pharmaceutically acceptable salts, solvates and prodrugs thereof in the preparation of a medicament for the treatment or prevention of cancer.

TAFIa inhibitors are efficacious in treatment of any condition in which fibrosis is a contributing factor. Suitable fibrotic conditions include cystic fibrosis, pulmonary fibrotic diseases such as chronic obstructive pulmonary disease (COPD), adult respiratory distress syndrome (ARDS), fibromuscular dysplasia and fibrotic lung disease, and fibrin deposition in the eye during opthalmic surgery. Accordingly, another preferred embodiment of the present invention provides for the use of compounds of formula (I) and pharmaceutically acceptable salts, solvates and prodrugs thereof in the preparation of a medicament for the treatment or prevention of fibrotic disease, and in particular for the treatment or prevention of a fibrotic condition selected from cystic fibrosis, pulmonary fibrotic diseases, chronic obstructive pulmonary disease (COPD), adult respiratory distress syndrome (ARDS), fibromuscular dysplasia, fibrotic lung disease and fibrin deposition in the eye during opthalmic surgery.

TAFIa inhibitors are efficacious in the treatment of inflammation, inflammatory diseases such as asthma, arthritis, endometriosis, inflammatory bowel diseases, psoriasis and atopic dermatitis and neurodegenerative diseases such as Alzheimer's disease and Parkinson's disease. Accordingly, another preferred embodiment of the present invention provides for the use of compounds of formula (I) and pharmaceutically acceptable salts, solvates and prodrugs thereof in the preparation of a medicament for the treatment or prevention of inflammation, inflammatory diseases such as asthma, arthritis, endometriosis, inflammatory bowel diseases, psoriasis and atopic dermatitis and neurodegenerative diseases such as Alzheimer's disease and Parkinson's disease.

TAFIa binds to and breaks down bradykinin (Tan et al., *Biochemistry* 1995, 34, 5811). There are many conditions which are known to benefit from maintaining or enhancing levels of bradykinin such as hypertension, angina, heart failure, pulmonary hypertension, renal failure and organ failure. Accordingly, another preferred embodiment of the present invention provides for the use of compounds of formula (I) and pharmaceutically acceptable salts, solvates and prodrugs thereof in the preparation of a medicament for the treatment or prevention of conditions which benefit from maintaining or enhancing levels of bradykinin.

In a further aspect, the present invention provides a method of treating or preventing thrombotic conditions, atherosclerosis, adhesions, dermal scarring, cancer, fibrotic conditions, inflammatory diseases and those conditions which benefit from maintaining or enhancing bradykinin levels in the body which comprises administering a therapeutically effective amount of a compound of formula (I) or a stereoisomer, tautomer or pharmaceutically acceptable salt, solvate or prodrug thereof to a patient in need of such treatment.

One preferred embodiment of the present invention provides for a method of treating or preventing thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and preventing cardiovascular events following intervention surgery which comprises administering a therapeutically effective amount of a compound of formula (I) or a stereoisomer, tautomer or pharmaceutically acceptable salt, solvate or prodrug thereof to a patient in need of such treatment. Subjects with thrombotic conditions who are suitable for treatment by the present invention include those having conditions associated with hypercoagulability, such as factor V mutation, antithrombin III deficiency, heparin cofactor II deficiency, protein C deficiency, protein S deficiency and polycythemia vera, and those exhibiting homocystinaemia or homocystinuria.

Another preferred embodiment of the present invention provides for a method of treating or preventing atherosclerosis which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing adhesions or dermal scarring which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing cancer which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing a fibrotic condition such as cystic fibrosis, pulmonary fibrotic diseases, chronic obstructive pulmonary disease (COPD), adult respiratory distress syndrome (ARDS), fibromuscular dysplasia, fibrotic lung disease and fibrin deposition in the eye during ophthalmic surgery which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing an inflammatory disease such as asthma, arthritis, endometriosis, inflammatory bowel diseases, psoriasis or atopic dermatitis or a neurodegenerative disease such as Alzheimer's disease or Parkinson's disease which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing conditions which benefit from maintaining or enhancing levels of bradykinin which comprises administering a therapeutically effective amount of a compound of formula (I) or a stereoisomer, tautomer or pharmaceutically acceptable salt, solvate or prodrug thereof to a patient in need of such treatment.

It is to be appreciated that all references herein to treatment include curative, palliative and prophylactic treatment.

The amount of compound administered and the frequency of administration will be determined by the attending physician taking into account the characteristics of the patient, such as age, weight and state of health, and the degree of inhibition of TAFIa desired. The total daily dose for a typical 70 kg adult will generally be between 1 mg and 5 g, preferably between 10 mg and 1 g, more preferably between 50 mg and 750 mg. The total dose may be given as a single or divided dose.

The compounds of the present invention may be used alone or in combination with other therapeutic agents. When used in combination with another therapeutic agent the administration of the two agents may be simultaneous or sequential. Simultaneous administration includes the administration of a single dosage form that comprises both agents and the administration of the two agents in separate dosage forms at substantially the same time. Sequential administration includes the administration of the two agents according to different schedules provided that there is an overlap in the periods during which the treatment is provided. Suitable agents with which the compounds of the formula (I) can be co-administered include antithrombotics, including antiplatelet agents, anticoagulants and profibrinolytics. Suitable antithrombotics include: aspirin, Plavix™, ticlopidine, warfarin (Coumadin™), unfractionated heparin, hirudin (Lepirudin™), streptokinase, urokinase, recombinant tissue plasminogen activator (tPA), dipyridamole, Reopro™, Aggrastat™, and Integrilin™. The compounds of the formula (I) can also be administered together with antihypertensive agents and with agents to treat dyslipidaemia such as statins eg Lipitor™. Further suitable drug classes for co-administration include Factor X inhibitors and antiarrhythmics such as amiodarone or digoxin. Accordingly, in a further aspect, the present invention provides for the use of a compound of formula (I) or a stereoisomer, tautomer or pharmaceutically acceptable salt, solvate or prodrug thereof in combination with an antithrombotic agent for the preparation of a medicament for the treatment of thrombosis. In a preferred embodiment the antithrombotic is an profibrinolytic. In a more preferred embodiment the antithrombotic is recombinant tissue plasminogen activator (tPA).

In a further aspect, the present invention provides for a method of treating or preventing thrombosis, which comprises administering a therapeutically effective amount of a compound of formula (I) or a stereoisomer, tautomer or pharmaceutically acceptable salt, solvate or prodrug thereof in combination with an antithrombotic to a patient in need of such treatment. In a preferred embodiment the antithrombotic is an profibrinolytic. In a more preferred embodiment the antithrombotic is recombinant tissue plasminogen activator (tPA).

In a further aspect, the present invention provides for a kit comprising:
 a. a composition comprising a compound of formula (I) or a stereoisomer, tautomer or pharmaceutically acceptable salt, solvate or prodrug thereof as disclosed herein and a pharmaceutically acceptable diluent or carrier;
 b. a composition comprising an antithrombotic and a pharmaceutically acceptable diluent or carrier; and
 c. a container The components of this kit may be administered separately, simultaneously or sequentially.

The present invention also provides for the use a compound of formula (I) or a stereoisomer, tautomer or pharmaceutically acceptable salt, solvate or prodrug thereof as a coating on intravascular devices such as indwelling catheters for dialysis, replacement heart valves or arterial stents; and as a coating on extra-corporeal blood circulation devices such as heart, lung and kidney dialysis machines, to prevent thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events such as restenosis following intervention surgery such as percutaneous transluminal coronary angioplasty, grafting, stent in-placement, coronary bypass surgery or any other forms of surgical revascularisation or intervention.

The invention provides for intravascular devices, of which the intravascular portion is coated with a compound of formula (I) or a stereoisomer, tautomer or pharmaceutically acceptable salt, solvate or prodrug thereof; and extra corporeal blood circulation devices such as heart, lung and kidney dialysis machines, where the portion coming into contact with the subjects blood is coated with a compound of formula (I) or a stereoisomer, tautomer or pharmaceutically acceptable salt, solvate or prodrug thereof.

The compounds of the present invention are TAFIa inhibitors, whose utility is based upon preventing the reaction between a developing thrombus and TAFIa. It has been found that the compounds of the present invention are also capable of binding to the unactivated TAFI molecule, at the site implicated in the reaction between TAFIa and the developing clot. The use of TAFIa inhibitors as described above in terms of scope and utility, includes such TAFIa inhibitors which bind to TAFI.

The invention is further illustrated by the following, non-limiting examples.

Melting points were determined on a Gallenkamp melting point apparatus using glass capillary tubes and are uncorrected. Unless otherwise indicated all reactions were carried out under a nitrogen atmosphere, using commercially available anhydrous solvents. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40–63 µm silica gel (Merck silica gel 60). Ion exchange chromatography was performed using with the specified ion exchange resin which had been pre-washed with deionised water. Proton NMR spectra were measured on a Varian Inova 300, Varian Inova 400, or Varian Mercury 400 spectrometer in the solvents specified. In the NMR spectra, only non-exchangeable protons which appeared distinct from the solvent peaks are reported. Low resolution mass spectra were recorded on either a Fisons Trio 1000, using thermospray positive ionisation, or a Finnigan Navigator, using electrospray positive or negative ionisation. High resolution mass spectra were recorded on a Bruker Apex II FT-MS using electrospray positive ionisation. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in a suitable solvent.

| Abbreviations and Definitions | |
|---|---|
| Arbocel ™ | Filtration agent, from J. Rettenmaier & Sohne, Germany |
| Amberlyst ® 15 | Ion exchange resin, available from Aldrich Chemical Company |
| atm | Pressure in atmospheres (1 atm = 760 Torr = 101.3 kPa) |
| Biotage ™ | Chromatography performed using Flash 75 silica gel cartridge, from Biotage, UK |
| BOC | tert-Butyloxycarbonyl group |
| br | Broad |
| c | Concentration used for optical rotation measurements in g per 100 ml (1 mg/ml is c 0.10) |
| cat | Catalytic |
| d | Doublet |
| dd | Doublet of doublets |
| Degussa ® 101 | 10 wt % palladium on activated carbon, Degussa type E101 available from Aldrich Chemical Company |
| Dowex ® | Ion exchange resin, from Aldrich Chemical Company |
| ee | Enantiomeric excess |
| HRMS | High Resolution Mass Spectrocopy (electrospray ionisation positive scan) |
| Hyflo ™ | Hyflo supercel ®, from Aldrich Chemical Company |
| liq | liquid |
| LRMS | Low Resolution Mass Spectroscopy (electrospray or thermospray ionisation positive scan) |
| LRMS (ES) | Low Resolution Mass Spectroscopy (electrospray ionisation negative scan) |
| m | Multiplet |
| m/z | Mass spectrum peak |
| MCI ™ gel | High porous polymer, CHP20P 75–150 μm, from Mitsubishi Chemical Corporation |
| psi | Pounds per square inch (1 psi = 6.9 kPa) |
| q | Quartet |
| $R_f$ | Retention factor on TLC |
| s | Singlet |
| Sep-Pak ® | Reverse phase $C_{18}$ silica gel cartridge, Waters Corporation |
| t | Triplet |
| TLC | Thin Layer Chromatography |
| δ | Chemical shift |

EXAMPLE 1

2-[(3S)-3-Aminopyrrolidinyl]-3-(1H-imidazol-4-yl)propanoic Acid

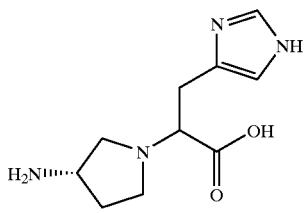

Hydrochloric acid (5 ml, 6M) was added to a solution of the acid from Preparation 48 (120 mg, 0.37 mmol) in water (3 ml), and the mixture was stirred for 3 hours. The solution was diluted with water (15 ml) and purified by column chromatography on Dowex® 50WX8 ion-exchange resin, using water:0.88 ammonia (95:5) as eluant to afford the title compound as a colourless foam, 70 mg. $^1$H-NMR ($D_2O$, 300 MHz) (mixture of diastereoisomers) δ: 1.78 (m, 1H), 2.20 (m, 1H), 2.68–2.97 (m, 5H), 3.02 (m, 1H), 3.26 (m, 1H), 3.74 (m, 1H), 6.83 (s, 1H), 7.63 (s, 1H). LRMS: m/z (ES$^+$) 247 [MNa$^+$].

Alternative Method:

Sodium hydroxide solution (0.8 ml, 5M) was added dropwise to an ice-cooled solution of the ester from Preparation 47 (400 mg, 0.86 mmol) in water (15 ml), and the mixture was then stirred at room temperature for 18 hours. The solution was purified by column chromatography on Dowex® 50WX8 ion-exchange resin, using an elution gradient of water:0.88 ammonia (100:0 to 95:5) to afford the title compound as a beige foam, 50 mg.

EXAMPLE 2

(+)-(2S)-2-[(3S)-3-Aminopyrrolidinyl]-3-(1H-imidazol-4-yl)propanoic Acid

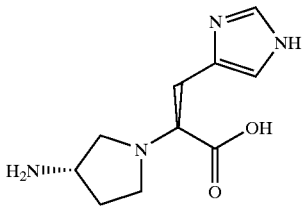

The protected amine from Preparation 55 (crude) was added to an ice-cooled solution of trifluoroacetic acid (6 ml) and water (1 ml), and the mixture was stirred at room temperature for 18 hours. The solution was evaporated under reduced pressure and the residue was suspended in water then washed with ether (3×20 ml). The aqueous solution was purified by column chromatography using Dowex® 50WX8 ion-exchange resin, and an elution gradient of water:0.88 ammonia (100:0 to 95:5) to afford the title compound as a colourless foam, 40 mg. $^1$H-NMR ($D_2O$, 300 MHz) δ: 1.78 (m, 1H), 2.22 (m, 1H), 2.77 (m, 2H), 2.94 (d, 2H), 3.03 (m, 2H), 3.27 (t, 1H), 3.77 (m, 1H), 6.86 (s, 1H), 7.65 (s, 1H). LRMS: m/z (ES$^+$) 225 [MH$^+$]. [α]$_D$=+16.93 (c=0.13, water)

EXAMPLE 3

(+)-(2S)-2-[(3R)-3-Aminopyrrolidinyl]-3-(1H-imidazol-4-yl)propanoic Acid

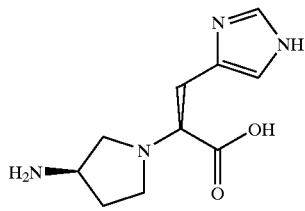

The title compound was obtained as a tan-coloured foam in 64% yield from the protected amino acid from Preparation 56 following the procedure described in Example 2. $^1$H-NMR (D$_2$O, 300 MHz) δ: 1.78 (m, 1H), 2.20 (m, 1H), 2.77–2.98 (m, 5H), 3.02 (m, 1H), 3.27 (t, 1H), 3.77 (m, 1H), 6.83 (s, 1H), 7.65 (s, 1H). LRMS: m/z (ES$^+$) 225 [MH$^+$]. [α]$_D$=+2.89 (c=0.034, water).

EXAMPLE 4

(+)-(2S)-2-[(3S)-3-Aminopyrrolidinyl]-3-(1-propyl-1H-imidazol-4-yl)propanoic Acid

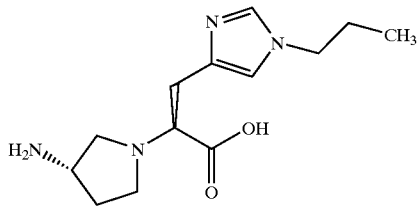

A mixture of the protected amine from Preparation 49 (1 g, 2.5 mmol) and 10% palladium on charcoal (250 mg) in water (60 ml) was hydrogenated at room temperature for 3 hours at 50 psi (345 kPa). The mixture was filtered through Arbocel® and the residue was washed with water. The filtrate was freeze-dried to afford the title compound as a solid, 560 mg. $^1$H-NMR (CD$_3$OD, 400 MHz) 67: 0.85 (t, 3H), 1.76 (m, 3H), 2.19 (m, 1H), 2.63 (m, 1H), 2.80 (m, 1H), 2.86–3.04 (m, 3H), 3.19 (m, 1H), 3.28 (m, 1H), 3.62 (m, 1H), 3.87 (t, 2H), 6.91 (s, 1H), 7.44 (s, 1H). LRMS: m/z (ES$^-$) 265 [M–H$^-$]. [α]$_D$=+18.3 (c=0.197, water). Found: C, 51.53; H, 8.16; N, 18.11. C$_{13}$H$_{22}$N$_4$O$_2$; 2H$_2$O requires C, 51.64; H, 8.67; N, 18.53%.

Alternative Method:

Sodium hydroxide solution (50 μl, 5M) was added dropwise to a solution of the ester from Preparation 46 (18 mg, 0.047 mmol) in dioxan (3 ml) and the solution was stirred at room temperature for 18 hours then concentrated under reduced pressure. The product was dissolved in water (4 ml), hydrochloric acid (3 ml, 6M) was added, and the solution was stirred at room temperature for 4 hours. The solution was diluted with water (10 ml) and purified by column chromatography on Dowex® WX8 ion-exchange resin, using an elution gradient of water:0.88 ammonia (100:0 to 95:5). The product was dissolved in water, filtered through silica gel, and the filtrate freeze-dried, to afford the title compound as a film, 2 mg. LRMS: m/z (ES$^+$) 267 [MH$^+$]

EXAMPLE 5

(2S)-2-[(3S)-3-Aminopyrrolidinyl]-3-(1-isopentyl-1H-imidazol-4-yl)propanoic Acid

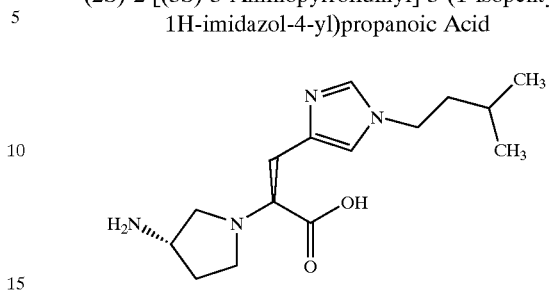

A mixture of the protected amine from Preparation 50 (1.3 g, 3 mmol) and 10% palladium on charcoal (Degussa® 101) in 2M hydrochloric acid (1.5 ml) and water (50 ml) was hydrogenated at 50 psi (345 kPa) and room temperature for 18 hours. The mixture was filtered through Arbocel®, and the filtrate was purified by column chromatography on Dowex® ion-exchange resin, using an elution gradient of water:0.88 ammonia (100:0 to 95:5). The product-containing fractions were evaporated under reduced pressure. The residue was dissolved in water (5 ml) and freeze-dried to afford the title compound as a fawn-coloured solid, 540 mg. $^1$H-NMR (CD$_3$OD, 300 MHz) δ: 0.95 (d, 6H), 1.57 (m, 1H), 1.63 (m, 2H), 1.80 (m, 1H), 2.20 (m, 1H), 2.66 (m, 1H), 2.82 (m, 1H), 2.90–3.10 (m, 4H), 3.22 (m, 1H), 3.68 (m, 1H), 3.98 (t, 2H), 6.98 (s, 1H), 7.52 (s, 1H). LRMS: m/z (TSP$^+$) 295.2 [MH$^+$]. Found: C, 58.50; H, 9.01; N, 18.06. C$_{15}$H$_{26}$N$_4$O$_2$;0.75H$_2$O requires C, 58.51; H, 9.00; N, 18.20%.

EXAMPLE 6

(+)-(2S)-2-[(3S)-3-Aminopyrrolidinyl]-3-[1-(2-cyclohexylethyl)-1H-imidazol-4-yl]propanoic Acid

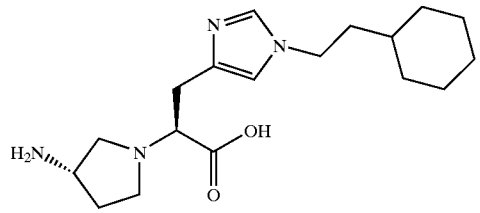

The title compound was obtained in 76% yield from the protected amine from Preparation 51, following a similar procedure to that described in Example 5. $^1$H-NMR (D$_2$O, 400 MHz) δ: 0.75 (m, 2H), 0.96 (m, 4H), 1.42 (m, 7H), 1.63 (m, 1H), 2.14 (m, 1H), 2.62 (m, 2H), 2.77 (d, 2H), 2.97 (m, 2H), 3.18 (t, 1H), 3.60 (m, 1H), 3.79 (t, 2H), 6.77 (s, 1H), 7.40 (s, 1H). LRMS: m/z (ES$^+$) 335 [MH$^+$]. [α]$_D$=+10.87 (c=0.127, water). Found: C, 59.79; H, 9.12; N, 15.51. C$_{18}$H$_{30}$N$_4$O$_2$; 1.5H$_2$O requires C, 59.81; N. 9.20; N, 15.50%.

EXAMPLE 7

(+)-(2S)-2-[(3S)-3-Aminopyrrolidinyl]-3-[1-(3-cyclohexylpropyl)-1H-imidazol-4-yl]propanoic Acid

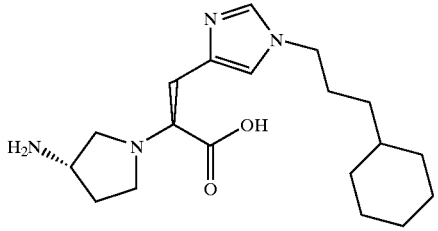

The title compound was obtained as a solid in 59% yield from the protected amine from Preparation 52, following a similar procedure to that described in Example 5. $^1$H-NMR (CD$_3$OD, 400 MHz) δ: 0.90 (m, 2H), 1.15–1.30 (m, 6H), 1.61–1.82 (m, 8H), 2.20 (m, 1H), 2.65 (m, 1H), 2.80–3.08 (m, 5H), 3.22 (m, 1H), 3.66 (m, 1H), 3.92 (t, 2H), 6.96 (s, 1H), 7.50 (s, 1H). LRMS: m/z (ES$^+$) 349 [MH$^+$]. [α]$_D$=+7.32 (c=0.109, water). Found: C, 59.32; H, 9.19; N, 14.39. C$_{19}$H$_{32}$N$_4$O$_2$; 2H$_2$O requires C, 59.35; N, 9.44; N, 14.57%.

EXAMPLE 8

(+)-(2S)-2-[(3S)-3-Aminopyrrolidinyl]-3-[1-(2-phenylethyl)-1H-imidazol-4-yl]propanoic Acid

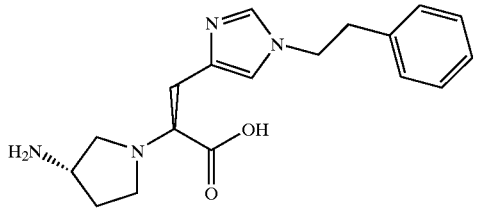

The title compound was obtained as a beige coloured solid in 68% yield from the protected amine from Preparation 53, following a similar procedure to that described in Example 5. $^1$H-NMR (D$_2$O, 400 MHz) δ: 1.70 (m, 1H), 2.18 (m, 1H), 2.60–2.82 (m, 4H), 2.92 (t, 2H), 3.00 (t, 2H), 3.20 (m, 1H), 3.65 (m, 1H), 4.08 (m, 2H), 6.78 (s, 1H), 6.98 (d, 2H), 7.18 (m, 4H). LRMS: m/z (ES$^+$) 329 [MH$^+$]. [α]$_D$=+25.83 (c=0.115, water). Found: C, 60.46; H, 7.58; N, 15.57. C$_{18}$H$_{24}$N$_4$O$_2$; 1.5H$_2$O requires C, 60.83; N, 7.66; N, 15.76%.

EXAMPLE 9

(+)-(2S)-2-[(3S)-3-Aminopyrrolidinyl]-3-[1-phenyl-1H-imidazol-4-yl]propanoic Acid

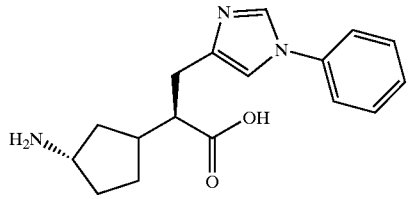

A mixture of the protected amine from Preparation 54 (56 mg, 0.13 mmol) and 5% Pd/C (Degussa®) in hydrochloric acid (0.05%, 30 ml) was hydrogenated at 50 psi and room temperature for 4 hours. The mixture was filtered through Arbocel® and the filtrate was purified by column chromatography on Dowex® ion-change resin using an elution gradient of water:0.88 ammonia (100:0 to 95:5). The product-containing fractions were evaporated and the residue was dissolved in water then freeze-dried to afford the title compound as a beige coloured powder, 19 mg. $^1$H-NMR (D$_2$O, 400 MHz) δ: 1.78 (m, 1H), 2.21 (m, 1H), 2.80 (m, 2H), 2.95 (m, 2H), 3.10 (m, 2H), 3.38 (m, 1H), 3.78 (m, 1H), 7.22 (s, 1H), 7.35 (m, 1H), 7.42 (m, 4H), 7.92 (s, 1H). HRMS: m/z (ES$^+$) 301.1653 [MH$^+$]. [α]$_D$=+5.88 (c=0.136, water). Found: C, 52.99; H, 6.90; N, 15.27. C$_{16}$H$_{20}$N$_4$O$_2$; 3.5H$_2$O requires C, 52.88; H, 7.49; N, 15.42%.

EXAMPLE 10

(+)-(2S)-2-[(3S)-3-aminopyrrolidinyl]-3-[1H-imidazol-4-yl]propanoic Acid

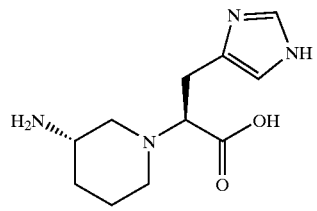

The title compound was obtained as a white solid in 74% yield from the protected imidazole from Preparation 57, following the procedure described in Example 2. $^1$H-NMR (D$_2$O, 400 MHz) δ: 1.43 (m, 2H), 1.74 (m, 1H), 1.86 (m, 1H), 2.41 (m, 2H), 2.77 (m, 2H), 2.92 (m, 2H), 3.24 (m, 2H), 6.80 (s, 1H), 7.64 (s, 1H). LRMS: m/z (ES$^+$) 239 [MH$^+$]. [α]$_D$=+1.77 (c=0.090, water).

Preparation 1

Methyl 2-bromo-3-(1H-imidazol-4-yl)propanoate

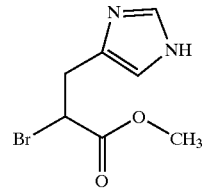

Hydrogen chloride was bubbled through an ice-cooled solution of 2-bromo-3-(1H-imidazol-4-yl)propanoic acid (500 mg, 2.3 mmol) in methanol (15 ml) for 10 minutes, and the mixture was stirred at room temperature for 18 hours. The solution was evaporated under reduced pressure, the residue was suspended in ice-cooled sodium bicarbonate solution, and the suspension was extracted with dichloromethane (4×20 ml). The combined organic solutions were dried (Na$_2$SO$_4$) and evaporated under reduced pressure to afford the title compound as an oil, 600 mg. $^1$H-NMR (CDCl$_3$, 300 MHz) δ: 3.24 (dd, 1H), 3.44 (dd, 1H), 3.78 (s, 3H), 4.58 (dd, 1H), 6.92 (s, 1H), 7.60 (s, 1H). LRMS: m/z (ES$^+$) 233, 235 [MH$^+$].

Preparation 2

Methyl 2-{(3S)-3-[(tert-butoxycarbonyl)amino]pyrrolidinyl}-3-(1H-imidazol-4-yl)propanoate

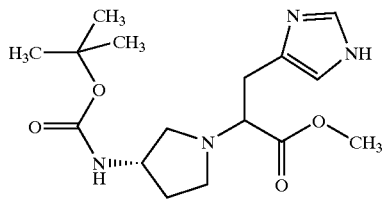

A mixture of the bromide from Preparation 1 (200 mg, 0.86 mmol), and (3S)-3-(-)-(tert-butyloxycarbonylamino)pyrrolidine (320 mg, 1.72 mmol) in acetonitrile (20 ml) was heated under reflux for 2 hours. The cooled solution was evaporated under reduced pressure and the residue was purified by column chromatography on silica gel using an elution gradient of dichloromethane:methanol (100:0 to 94:6) to give an oil. This product was dissolved in ethyl acetate and extracted with water (3×20 ml). The combined aqueous extracts were then re-extracted with dichloromethane (3×20 ml), and these combined organic extracts dried ($Na_2SO_4$) and evaporated under reduced pressure to afford the title compound as an oil, 180 mg. $^1$H-NMR (CDCl$_3$, 300 MHz) δ: 1.42 (s, 9H), 1.66 (m, 1H), 2.19 (m, 1H), 2.60–2.80 (m, 2H), 2.90–3.02 (m, 3H), 3.10 (m, 1H), 3.61 (t, 1H), 3.66 (s, 3H), 4.14 (m, 1H), 4.86–5.00 (m, 1H), 6.81 (s, 1H), 7.56 (s, 1H). LRMS: m/z (ES$^+$) 339.2 [MH$^+$]. HRMS: 339.2027 [MH$^+$], $C_{16}H_{26}N_4O_4$=338.41.

Preparation 3

Methyl (2S)-2-[(tert-butoxycarbonyl)amino]-3-(1-propyl-1H-imidazol-4-yl)propanoate

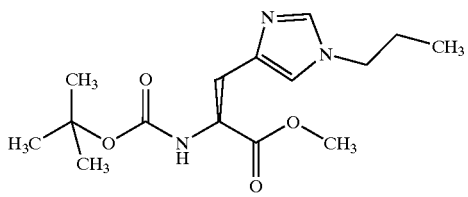

n-Propyl bromide (0.17 ml, 1.85 mmol) was added to a mixture of N$^\alpha$-Boc-L-histidine methyl ester (500 mg, 1.85 mmol) and potassium carbonate (200 mg, 1.85 mmol) in acetonitrile (20 ml), and the mixture was heated under reflux for 18 hours. TLC analysis showed starting material remaining, so additional n-propyl bromide (0.17 ml, 1.85 mmol) and potassium carbonate (200 mg, 1.85 mmol) were added, and the mixture was heated for a further 8 hours. The cooled, mixture was concentrated under reduced pressure. The residue was dissolved in water and the solution was extracted with ethyl acetate (3×20 ml). The combined organic extracts were washed with brine (3×20 ml), dried ($Na_2SO_4$) and evaporated under reduced pressure. The residual orange oil was purified by column chromatography on silica gel using an elution gradient of hexane:ethyl acetate (100:0 to 0:100) to afford the title compound as a colourless oil, 200 mg. $^1$H-NMR (CDCl$_3$, 300 MHz) δ: 0.90 (t, 3H), 1.42 (s, 9H), 1.78 (m, 2H), 3.03 (m, 2H), 3.68 (s, 3H), 3.80 (t, 2H), 4.56 (m, 1H), 5.92 (m, 1H), 6.65 (s, 1H), 7.37 (s, 1H). LRMS: m/z (TSP$^+$) 312.2 (MH$^+$).

Preparation 4

(−)-Methyl (2S)-2-[(tert-butoxycarbonyl)amino]-3-(1-isopentyl-1H-imidazol-4-yl)propanoate

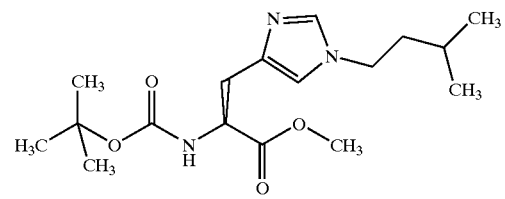

1-Bromo-3-methylbutane (4.44 ml, 37.2 mmol) was added to a mixture of N$^\alpha$-Boc-L-histidine methyl ester (5.0 g, 18.6 mmol) and sodium carbonate (4.0 g, 37.2 mmol) in acetonitrile (80 ml), and the mixture was heated under reflux for 18 hours. The cooled mixture was concentrated under reduced pressure. The residue was suspended in water and the suspension was basified using sodium carbonate then extracted with ethyl acetate (3×30 ml). The combined organic extracts were dried ($Na_2SO_4$) and evaporated under reduced pressure. The residual oil was purified by column chromatography on silica gel using an elution gradient of hexane:ethyl acetate (100:0 to 5:95) to afford the title compound as a colourless oil, 2.8 g. $^1$H-NMR (CDCl$_3$, 400 MHz) δ: 0.90 (d, 6H), 1.40 (s, 9H), 1.50 (m, 1H), 1.60 (m, 2H), 2.96–3.06 (m, 2H), 3.62 (s, 3H), 3.82 (t, 2H), 4.50 (m, 1H), 5.85 (m, 1H), 6.62 (s, 1H), 7.32 (s, 1H). LRMS: m/z (ES$^+$) 340 [MH$^+$]. [α]$_D$=−2.3 (c=0.22, methanol).

Preparation 5

(−)-Methyl (2S)-2-[(tert-butoxycarbonyl)amino]-3-[1-(2-cyclohexylethyl)-1H-imidazol-4-yl]propanoate

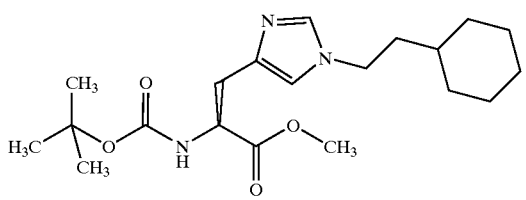

The title compound was obtained as a colourless oil in 46% yield from N$^\alpha$-Boc-L-histidine methyl ester and 2-cyclohexylethyl bromide, following the procedure described in Preparation 4. $^1$H-NMR (CDCl$_3$, 400 MHz) δ: 0.90 (m, 2H), 1.17 (m, 4H), 1.40 (s, 9H), 1.57–1.68 (m, 7H), 2.96–3.06 (m, 2H), 3.62 (s, 3H), 3.82 (t, 2H), 4.50 (m, 1H), 5.83 (m, 1H), 6.60 (s, 1H), 7.30 (s, 1H). LRMS: m/z (ES$^+$) 380 [MH$^+$]. [α]$_D$=−1.13 (c=0.19, methanol).

Preparation 6

(−)-Methyl (2S)-2-[(tert-butoxycarbonyl)amino]-3-[1-(2-phenylethyl)-1H-imidazol-4-yl]propanoate

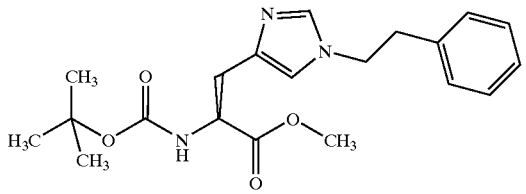

The title compound was obtained as a colourless oil in 41% yield from $N^{\alpha}$-Boc-L-histidine methyl ester and phenethyl bromide, following the procedure described in Preparation 4. $^1$H-NMR (CDCl$_3$, 400 MHz) δ: 1.40 (s, 9H), 2.98 (m, 4H), 3.64 (s, 3H), 4.05 (t, 2H), 4.48 (m, 1H), 5.80 (m, 1H), 6.58 (s, 1H), 7.00 (d, 2H), 7.16 (s, 1H), 7.22 (m, 3H). LRMS: m/z (ES$^+$) 374 [MH$^+$]. [α]$_D$=−12.28 (c=0.078, methanol).

Preparation 7

(−)-Methyl (2S)-2-amino-3-(1-propyl-1H-imidazol-4-yl)propanoate

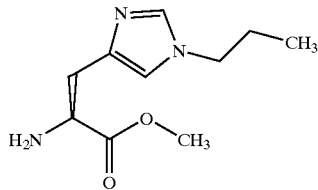

A solution of the protected amine from Preparation 3 (50 mg, 0.161 mmol) in 95% formic acid (3 ml) was stirred at room temperature for 3 days. The solution was concentrated under reduced pressure and the residue was purified by column chromatography on silica gel using dichloromethane:methanol:0.88 ammonia (90:10:1) as eluant to afford the title compound as an oil, 40 mg. $^1$H-NMR (CDCl$_3$, 300 MHz) δ: 0.94 (t, 3H), 1.58 (m, 2H), 2.87 (dd, 1H), 3.06 (dd, 1H), 3.75 (s, 3H), 3.83 (m, 3H), 6.72 (s, 1H), 7.40 (s, 1H). LRMS: m/z (ES$^+$) 334 [MNa$^+$]. [α]$_D$=−11.9 (c=0.15, methanol).

Preparation 8

(+)-Methyl (2S)-2-amino-3-(1-isopentyl-1H-imidazol-4-yl)propanoate dihydrochloride

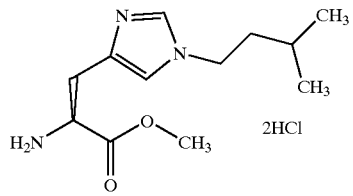

Hydrogen chloride was bubbled through a solution of the protected amine from Preparation 4 (2.8 g, 8.2 mmol) in diethyl ether (80 ml) at 5° C. for 20 minutes, and the resulting suspension was stirred at room temperature for 18 hours. The mixture was concentrated under reduced pressure and azeotroped with methanol then diethyl ether to afford the title compound as a viscous oil, 2.2 g. $^1$H-NMR (CD$_3$OD, 400 MHz) δ: 0.98 (d, 6H), 1.60 (m, 1H), 1.78 (m, 2H), 3.38 (m, 2H), 3.82 (s, 3H), 4.22 (t, 2H), 4.42 (t, 1H), 7.60 (s, 1H), 8.98 (s, 1H). LRMS: m/z (ES$^+$) 240 [MH$^+$]. [α]$_D$=+20.3 (c=0.16, methanol).

Preparation 9

(+)-Methyl (2S)-2-amino-3-[1-(2-cyclohexylethyl)-1H-imidazol-4-yl]propanoate

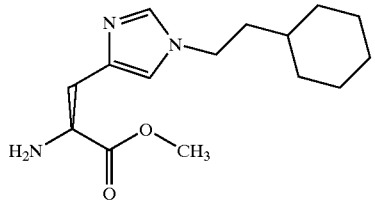

Hydrogen chloride was bubbled through a solution of the protected amine from Preparation 5 (6.4 g, 16.8 mmol) in diethyl ether (120 ml) at 5° C. for 20 minutes, and the resulting suspension was stirred at room temperature for 18 hours. The mixture was concentrated under reduced pressure and azeotroped with methanol then diethyl ether to give a colourless gum. This was suspended in a minimum volume of sodium bicarbonate solution and extracted with dichloromethane (4×30 ml). The combined organic extracts were washed with brine (20 ml), dried (Na$_2$SO$_4$) and evaporated under reduced pressure to afford the title compound as a colourless oil, 4.25 g. $^1$H-NMR (CDCl$_3$ 400 MHz) δ: 0.98 (d, 3H), 1.20 (m, 5H), 1.64 (m, 5H), 2.83 (dd, 1H), 3.02 (dd, 1H), 3.74 (s, 3H), 3.81 (m, 1H), 3.87 (t, 2H), 6.71 (s, 1H), 7.38 (s, 1H). LRMS: m/z (ES$^+$) 280 [MH$^+$]. [α]$_D$=+10.98 (c=0.19, methanol).

Preparation 10

(+)-Methyl (2S)-2-amino-3-[1-(2-phenylethyl)-1H-imidazol-4-yl]propanoate

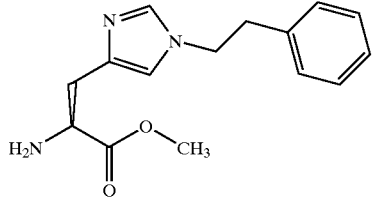

Hydrogen chloride was bubbled through a solution of the protected amine from Preparation 6 (5.6 g, 15.0 mmol) in diethyl ether (100 ml) at 5° C., and the resulting suspension was stirred at room temperature for 18 hours. The mixture was concentrated under reduced pressure and azeotroped with methanol then diethyl ether to give the hydrochloride salt of the title compound as a foam. A sample (500 mg) was dissolved in water, then neutralised using sodium bicarbonate and this solution was extracted with dichloromethane (6×15 ml). The combined organic extracts were dried (Na$_2$SO$_4$), concentrated under reduced pressure and azeotroped with diethyl ether to give a colourless oil, 250 mg. $^1$H-NMR (CDCl$_3$ 400 MHz) δ: 2.83 (dd, 1H), 3.02 (m, 3H), 3.75 (s, 3H), 3.81 (dd, 1H), 4.14 (t, 2H), 6.63 (s, 1H), 7.05 (d, 2H), 7.25 (m, 4H). LRMS: m/z (TSP⁺) 274.2 [MH⁺]. [α]$_D$=+3.85 (c=0.156, methanol).

Preparation 11

Dimethyl (2S)-2-{[(benzyloxy)carbonyl]amino}butanedioate

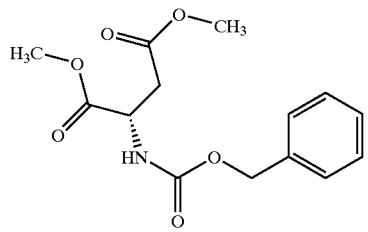

Hydrogen chloride was bubbled through a solution of N-benzyloxycarbonyl-L-aspartic acid (50 g, 185 mmol) in methanol (1 L) at 5° C. for 30 minutes, and the solution was stirred at room temperature for 18 hours. The mixture was concentrated under reduced pressure. The residue was dissolved in ethyl acetate (250 ml) and the resulting solution was washed with 5% aqueous sodium bicarbonate solution (3×100 ml) then brine (2×100 ml), dried (Na$_2$SO$_4$) and evaporated under reduced pressure to afford the title compound as a colourless oil, 54 g. ¹H-NMR (CDCl$_3$, 300 MHz) δ: 2.84 (dd, 1H), 3.02 (dd, 1H), 3.67 (s, 3H), 3.78 (s, 3H), 4.63 (m, 1H), 5.16 (s, 2H), 5.67 (m, 1H), 7.38 (m, 5H). LRMS: m/z (ES⁺) 318.1 [MNa⁺].

Preparation 12

(−)-Benzyl (1S)-3-hydroxy-1-(hydroxymethyl)propylcarbamate

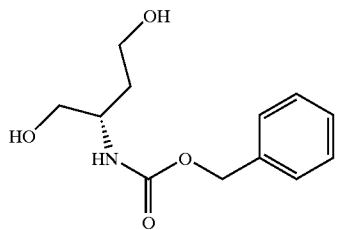

Sodium borohydride (13.77 g, 360 mmol) was added to a solution of the diester from Preparation 11 (54 g, 180 mmol) in tetrahydrofuran (320 ml), and the mixture was warmed to 45° C. Methanol (14 ml) was added, causing an exotherm (to 64° C.), and the mixture was stirred for 45 minutes. Additional methanol (28 ml) was added dropwise so as to maintain a temperature of 50–55° C., and once addition was complete, the reaction was stirred for a further hour, then cooled to room temperature. The mixture was chilled, diluted with water (100 ml) and 5% aqueous sodium bicarbonate solution (100 ml) and then extracted with ethyl acetate (3×200 ml). The combined organic solutions were washed with brine (3×100 ml), dried (Na$_2$SO$_4$) and evaporated under reduced pressure. The residual oil was crystallised with hexane, to afford the title compound as a colourless solid, 43 g. ¹H-NMR (CDCl$_3$, 300 MHz) δ: 1.67 (m, 1H), 1.82 (m, 1H), 2.56 (bs, 1H), 2.82 (bs, 1H), 3.60–3.80 (m, 4H), 3.94 (bs, 1H), 5.10 (s, 2H), 5.30 (m, 1H), 7.38 (m, 5H). [α]$_D$=−27.03 (c=0.145, ethanol).

Preparation 13

(+)-Benzyl (4S)-4-(2-hydroxyethyl)-2,2-dimethyl-1,3-oxazolidine-3-carboxylate

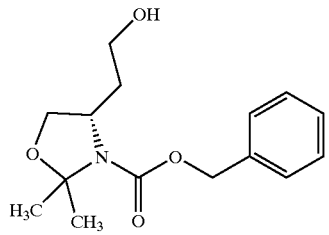

p-Toluenesulphonic acid monohydrate (16 g, 8.4 mmol) was added to a solution of the alcohol from Preparation 12 (20 g, 84 mmol) and 2,2-dimethoxypropane (100 ml) in dichloromethane (400 ml), and the mixture was stirred at room temperature for 18 hours. The mixture was washed with sodium bicarbonate solution (3×100 ml) and brine (3×100 ml), then dried (Na$_2$SO$_4$) and evaporated under reduced pressure. The residual oil was purified by column chromatography on silica gel using an elution gradient of ethyl acetate:hexane (30:70 to 100:0). The product was azeotroped further with diethyl ether to afford the title compound as a colourless thick oil, 10.4 g. ¹H-NMR (CD$_3$OD, 300 MHz) δ: 1.45 (s, 3H), 1.58 (s, 3H), 1.78 (m, 1H), 1.95 (m, 1H), 3.58 (m, 2H), 3.88 (m, 1H), 4.01 (m, 2H), 5.15 (s, 2H), 7.38 (m, 5H). LRMS: m/z (ES⁺) 302 [MNa⁺]. [α]$_D$=+13.34 (c=0.105, methanol)

Preparation 14

(+)-Benzyl (4S)-2,2-dimethyl-4-(2-oxoethyl)-1,3-oxazolidine-3-carboxylate

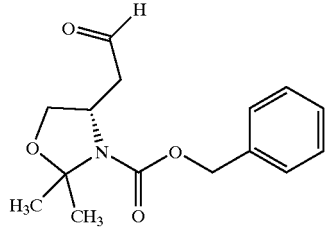

Pyridinium chlorochromate (13.9 g, 64.4 mmol) was added to absolution of the alcohol from Preparation 13 (9.0 g, 32.2 mmol) in dichloromethane (150 ml), and the mixture was stirred for 2.5 hours. Diethyl ether (150 ml) was added and the mixture was stirred for a further 5 minutes, then filtered through silica gel. The residue was washed with dichloromethane:diethyl ether (50:50, 200 ml). The combined filtrates were evaporated under reduced pressure, and the residual orange oil was purified by column chromatography on silica gel using an elution gradient of hexane:ethyl acetate (100:0 to 80:20), to afford the title compound as a colourless oil, 6.1 g. ¹H-NMR (CDCl$_3$, 300 MHz) (mixture of rotamers) δ: 1.55 (2xs, 6H), 2.72 (m, 1H), 2.88 (m, 0.5H), 3.06 (m, 0.5H), 3.78 (2xm, 1H), 4.08 (m, 1H), 4.38 (m, 1H), 5.14 (2xs, 2H), 7.38 (m, 5H), 9.70 (s, 0.5H), 9.80 (s, 0.5H). LRMS: m/z (TSP⁺) 277.9 [MH⁺]. [α]$_D$=+23.0 (c=0.216, dichloromethane).

Preparation 15

(+)-Benzyl (4S)-4-[2-({(1S)-1-methoxycarbonyl-2-(1-propyl-1H-imidazol-4-yl)ethyl}amino)ethyl]-2,2-dimethyl-1,3-oxazolidine-3-carboxylate

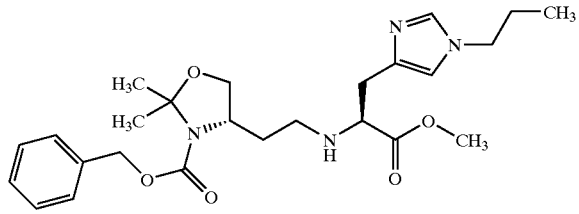

A solution of the imidazole from Preparation 7 (1.28 g, 4.5 mmol) in methanol (15 ml) was added to a solution of the aldehyde from Preparation 14 (1.25 g, 4.5 mmol) and sodium acetate (1.48 g, 18.0 mmol) in methanol (30 ml). 3 Å Molecular sieves were added, followed by sodium cyanoborohydride (570 mg, 9.1 mmol) portionwise, and the mixture was stirred at room temperature for 18 hours. Saturated ammonium chloride solution (10 ml) was added and the mixture was stirred for 5 minutes, then concentrated under reduced pressure. The residue was suspended in a mixture of saturated sodium bicarbonate solution and ethyl acetate, the suspension was filtered through Hyflo®, and the filtrate was separated. The aqueous phase was extracted with ethyl acetate (2×30 ml) and the combined organic extracts were dried ($Na_2SO_4$) and evaporated under reduced pressure. The residual oil was purified by column chromatography on silica gel using an elution gradient of dichloromethane:methanol (100:0 to 94:6). The product-containing fractions were concentrated under reduced pressure, the residue was suspended in 0.5M hydrochloric acid for 5 minutes, then the solution was neutralised using sodium bicarbonate. This solution was extracted with ethyl acetate (3×30 ml) and the combined organic extracts were dried ($Na_2SO_4$) and evaporated under reduced pressure to afford the title compound as a colourless oil, 1.0 g. $^1$H-NMR (CD$_3$OD, 300 MHz) δ:0.86 (t, 3H), 1.40–1.58 (m, 6H), 1.68–1.82 (m, 4H), 2.422.64 (m, 2H), 2.78–2.94 (m, 2H), 3.52 (m, 1H), 3.62 (s, 3H), 3.78 (m, 1H), 3.94 (m, 4H), 5.12 (s, 2H), 6.60 (s, 1H), 7.38 (m, 5H), 7.55 (s, 1H). LRMS: m/z (ES$^+$) 474 [MH$^+$]. [α]$_D$=+8.19 (c=0.159, dichloromethane).

Preparation 16

(+)-Benzyl (4S)-4-[2-({(1S)-1-(1-isopentyl-1H-imidazol-4-yl)-2-methoxycarbonylethyl}amino)ethyl]-2,2-dimethyl-1,3-oxazolidine-3-carboxylate

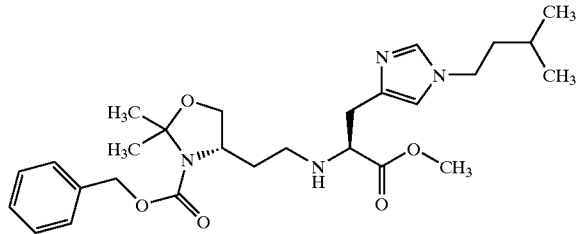

A solution of the imidazole from Preparation 8 (1.51 g, 4.8 mmol) in methanol (10 ml) was added to a solution of the aldehyde from Preparation 14 (1.34 g, 4.8 mmol) and sodium acetate (1.59 g, 18.0 mmol) in methanol (30 ml). 4 Å Molecular sieves were added, followed by sodium cyanoborohydride (610 mg, 9.3 mmol) portionwise, and the mixture was stirred at room temperature for 18 hours. 2M Hydrochloric acid (20 ml) was added and the mixture was stirred for 30 minutes then evaporated under reduced pressure. The residue was suspended in water, the suspension was acidified to pH 2 using 2M hydrochloric acid and filtered through Hyflo®, and the filtrate was neutralised using sodium bicarbonate then extracted with ethyl acetate (3×50 ml). The combined organic extracts were washed with brine (3×50 ml), dried ($Na_2SO_4$) and evaporated under reduced pressure. The residual oil was purified twice by column chromatography on silica gel using an elution gradient of dichloromethane:methanol:0.88 ammonia (99.8:0:0.2 to 95.8:4:0.2) to afford the title compound as a colourless oil, 930 mg. $^1$H-NMR (CDCl$_3$, 400 MHz) (mixture of rotamers) δ: 0.88 (2xs, 6H), 1.39–1.70 (m, 10H), 1.77–1.98 (m, 1H), 2.42 (m, 1H), 2.60 (m, 1H), 2.81 (m, 2H), 3.52 (m, 1H), 3.61 (s, 3H), 3.70 (d, 1H), 2.80 (m, 3H), 3.97 (m, 1H), 5.07 (m, 2H), 6.56–6.665 (2xs, 1H), 7.28 (m, 6H). LRMS: m/z (ES$^+$) 501 [MH$^+$]. [α]$_D$=+14.8 (c=0.135, methanol).

Preparation 17

(+)-Benzyl (4S)-4-{2-[((1S)-2-[1-(2-cyclohexylethyl)-1H-imidazol-4-yl]-1-methoxycarbonylethyl)amino]ethyl}-2,2-dimethyl-1,3-oxazolidine-3-carboxylate

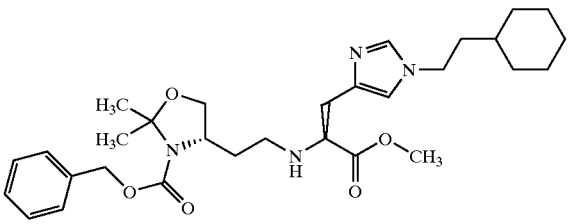

A solution of the aldehyde from Preparation 14 (3.97 g, 14 mmol) in dichloromethane (20 ml) was added to a solution of the imidazole from Preparation 9 (4 g, 14 mmol) and acetic acid (0.81 ml, 14 mmol) in dichloromethane (80 ml), and the solution was stirred for 40 minutes. Sodium triacetoxyborohydride (4.55 g, 21 mmol) was added and the mixture was stirred at room temperature for 18 hours. The solution was washed with sodium bicarbonate solution and brine (90 ml), then dried ($Na_2SO_4$) and evaporated under reduced pressure. The residual oil was purified by column chromatography on silica gel using an elution gradient of dichloromethane:methanol:0.88 ammonia (99.8:0.2 to 96.8:3:02). The product was azeotroped with diethyl ether to afford the title compound as a pale yellow oil, 4.5 g. $^1$H-NMR (CDCl$_3$, 400 MHz) (mixture of rotamers) δ:0.90 (m, 2H), 1.17 (m, 4H), 1.39–1.50 (m, 4H), 1.50–1.77 (m, 11H), 2.38–2.50 (m, 1H), 2.60 (m, 1H), 2.81 (m, 2H), 3.52 (m, 1H), 3.61 (m, 3H), 3.77 (d, 1H), 3.81 (m, 3H), 3.98 (m, 1H), 5.08 (m, 2H), 6.58–6.64 (m, 1H), 7.29 (m, 6H). [α]$_D$=+13.4 (c=0.103, methanol).

Preparation 18

(+)-Benzyl (4S)-4-{2-[((1S)-1-methoxycarbonyl-2-[1-(2-phenylethyl)-1H-imidazol-4-yl]-ethyl)amino)ethyl]-2,2-dimethyl-1,3-oxazolidine-3-carboxylate

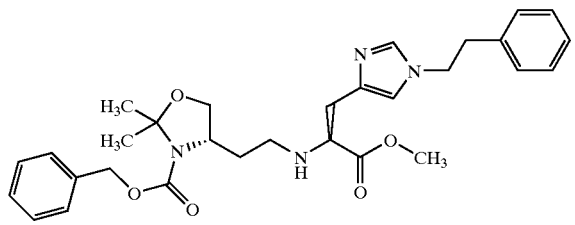

The title compound was obtained as a colourless oil in 56% yield from the aldehyde from Preparation 14 and the imidazole from Preparation 10, following a similar procedure to that described in Preparation 17. $^1$H-NMR (CDCl$_3$, 400 MHz) (mixture of rotamers) δ: 1.38–1.70 (m, 7H), 1.78–1.98 (m, 1H), 2.42 (m, 1H), 2.60 (m, 1H), 2.80 (m, 2H), 2.98 (m, 2H), 3.50 (m, 1H), 3.60 (s, 3H), 3.76 (m, 1H), 3.84 (m, 1H), 4.00 (m, 3H), 5.08 (m, 2H), 6.52, 6.60 (2xs, 1H), 7.00 (m, 2H), 7.14–7.37 (m, 9H). LRMS: m/z (ES$^+$) 535 [MH$^+$]. [α]$_D$=+12.59 (c=0.075, methanol).

Preparation 19

(+)-Benzyl (4S)-4-[2-({(1S)-1-methoxycarbonyl-2-[(1-trityl-1H-imidazol-4-yl)]ethyl}amino)ethyl]-2,2-dimethyl-1,3-oxazolidine-3-carboxylate

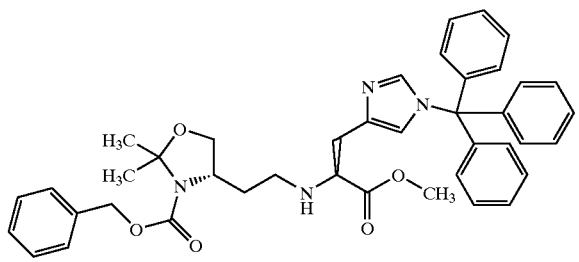

Methyl (2S)-2-amino-3-(1-trityl-1H-imidazol-4-yl)propanoate hydrochloride (12.2 g, 27 mol) was suspended in water and the solution was basified using sodium bicarbonate solution then extracted with dichloromethane (3×200 ml). The combined organic extracts were washed with brine (100 ml), dried (Na$_2$SO$_4$) and evaporated under reduced pressure to give an oil, 11.1 g. The oil was dissolved in dichloromethane (160 ml), MgSO$_4$ (20 g) and a solution of the aldehyde from Preparation 14 (7.5 g, 27 mmol) in dichloromethane (40 ml) were added, and the mixture was stirred at room temperature for 40 minutes then filtered. Sodium triacetoxyborohydride (8.6 g, 40 mmol) was added to the filtrate and the mixture was stirred at room temperature for 18 hours. The solution was diluted with saturated sodium bicarbonate solution and the mixture was extracted with dichloromethane (2×200 ml). The combined organic extracts were washed with brine (3×100 ml), dried (Na$_2$SO$_4$) and evaporated under reduced pressure. The residual oil was purified by column chromatography on silica gel using an elution gradient of dichloromethane:methanol:0.88 ammonia (99.8:0:0.2 to 95.8:4:0.2) to afford the title compound as a yellow oil, 18 g. $^1$H-NMR (CDCl$_3$, 400 MHz) δ: 1.40 (m, 1H), 1.46 (m, 3H), 1.59 (s, 2H), 1.62 (m, 1H), 1.78 (m, 1H), 2.37–2.63 (m, 2H), 2.76–2.86 (m, 2H), 3.45 (m, 1H), 3.58 (s, 3H), 3.72 (m, 1H), 3.81 (m, 1H), 3.98 (m, 1H), 5.02–5.14 (m, 2H), 6.50 (m, 1H), 7.08 (m, 6H), 7.28 (m, 15H). LRMS: m/z (ES$^+$) 673.5 [MH$^+$]. [α]$_D$=+18.76 (c=0.209, methanol).

Preparation 20

(+)-Methyl (2S)-2-[((3S)-3-{[(benzyloxy)carbonyl]amino}-4-hydroxybutyl)amino]-3-(1-propyl-1H-imidazol-4-yl)propanoate

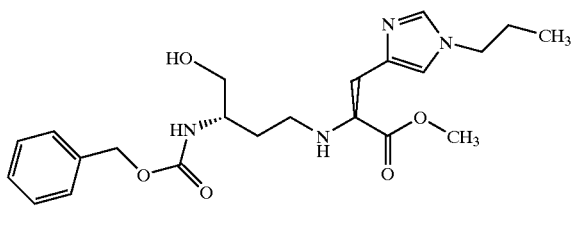

Hydrogen chloride was bubbled through an ice-cooled solution of the ester from Preparation 15 (1 g, 2.1 mmol) in dioxan (10 ml) for 25 minutes, then the mixture was stirred at room temperature for 18 hours. The solution was evaporated under reduced pressure, the residual foam was dissolved in water and the solution was basified using sodium bicarbonate solution then extracted with dichloromethane (3×20 ml). The combined organic solutions were washed with brine (20 ml), dried (Na$_2$SO$_4$) and evaporated under reduced pressure. The residual oil was purified by column chromatography on silica gel using dichloromethane:methanol:0.88 ammonia (99.8:0:0.2 to 96:4:0.2) to afford the title compound as a gum, 520 mg. $^1$H-NMR (CDCl$_3$, 400 MHz) δ: 0.88 (t, 3H), 1.74 (m, 2H), 1.98 (m, 1H), 2.55 (m, 1H), 2.75 (m, 1H), 2.90 (m, 2H), 3.58 (m, 3H), 3.70 (s, 3H), 3.78 (m, 3H), 5.08 (s, 2H), 5.77 (m, 1H), 6.64 (s, 1H), 7.34 (m, 6H). LRMS: m/z (ES$^+$) 433 [MH$^+$]. [α]$_D$=+17.12 (c=0.11, dichloromethane).

Preparation 21

(−)-Methyl (2S)-2-[((3S)-3-{[(benzyloxy)carbonyl]amino}-4-hydroxybutyl)amino]-3-(1-isopentyl-1H-imidazol-4-yl)propanoate A solution of the ester from Preparation 16 (930 mg, 1.86 mmol) in dioxan (30 ml) and concentrated hydrochloric acid (1 ml) was stirred at room temperature for 1 hour, cooled, diluted with water (15 ml), then concentrated under reduced pressure below 35° C. to remove the dioxan. The residue was diluted with water (15 ml) then basified using sodium bicarbonate, and the mixture was extracted with dichloromethane (3×50 ml). The combined organic extracts were dried (Na$_2$SO$_4$) and evaporated under reduced pressure. The residual oil was purified by column chromatography on silica gel using an elution gradient of dichloromethane:methanol:0.88 ammonia (99.8:0:0.2 to 95.8:4:0.2) to afford the title compound as a colourless oil, 630 mg. $^1$H-NMR (CDCl$_3$, 400 MHz) δ: 0.85 (d, 6H), 1.45–1.60 (m, 6H), 1.92 (m, 1H), 2.50 (m, 1H), 2.68 (m, 1H), 2.83 (m, 2H), 3.58 (m, 3H), 3.64 (s, 3H), 3.79 (m, 3H), 5.02 (m, 2H), 5.74 (m, 1H), 6.61 (s, 1H), 7.30 (m, 6H). LRMS: m/z (ES$^+$) 461 [MH$^+$]. [α]$_D$=−6.79 (c=0.165, methanol).

Preparation 22

(−)-Methyl (2S)-2-[((3S)-3-{[(benzyloxy)carbonyl]amino}-4-hydroxybutyl)amino]-3-[1-(2-cyclohexylethyl)-1H-imidazol-4-yl]propanoate

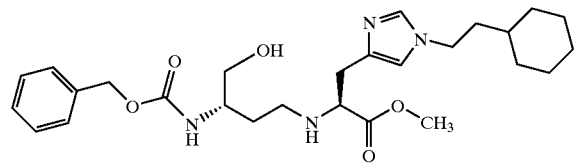

The title compound was obtained as a colourless oil in 77% yield from the ester from Preparation 17, following the procedure described in Preparation 21. $^1$H-NMR (CDCl$_3$, 400 MHz) δ: 0.90 (m, 2H), 1.17 (m, 4H), 1.48–168 (m, 8H), 1.96 (m, 1H), 2.46 (m, 1H), 2.68 (m, 1H), 2.84 (m, 2H), 3.57 (m, 3H), 3.64 (s, 3H), 3.78 (m, 3H), 5.02 (dd, 2H), 5.74 (m, 1H), 6.60 (s, 1H), 7.28 (m, 6H). LRMS: m/z (ES$^+$) 501 [MH$^+$]. [α]$_D$=−7.48 (c=0.163, methanol).

Preparation 23

Methyl (2S)-2-[((3S)-3-{[(benzyloxy)carbonyl]amino}-4-hydroxybutyl)amino]-3-[1-(2-phenylethyl)-1H-imidazol-4-yl]propanoate

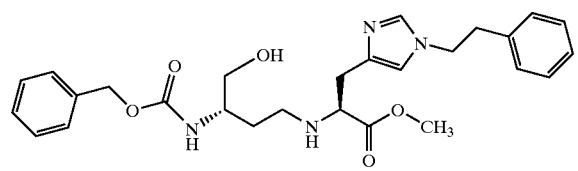

The title compound was obtained as a colourless oil in 86% yield from the ester from Preparation 18, following the procedure described in Preparation 21. $^1$H-NMR (CDCl$_3$, 400 MHz) δ: 1.50–1.70 (m, 3H), 1.95 (m, 1H), 2.50 (m, 1H), 2.90 (m, 1H), 2.83 (m, 2H), 2.96 (t, 2H), 3.57 (m, 3H), 3.63 (s, 3H), 3.78 (m, 3H), 4.00 (t, 2H), 5.03 (dd, 2H), 5.72 (m, 1H), 6.58 (s, 1H), 7.00 (d, 2H), 7.15 (s, 1H), 7.19–7.34 (m, 8H). LRMS: m/z (ES$^+$) 501 [MH$^+$]. [α]$_D$=−6.41 (c=0.088, methanol).

Preparation 24

(−)-Methyl (2S)-2-[((3S)-3-{[(benzyloxy)carbonyl]amino}-4-hydroxybutyl)amino]-3-(1-trityl-1H-imidazol-4-yl)propanoate

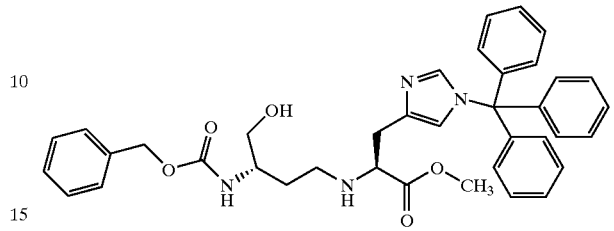

The title compound was obtained as a foam after evaporation from diethyl ether in 42% yield from the ester from Preparation 19, following a similar procedure to that described in Preparation 21. $^1$H-NMR (CDCl$_3$, 400 MHz) δ: 1.46–1.66 (m, 3H), 1.98 (m, 1H), 2.48 (m, 1H), 2.70 (m, 1H), 2.85 (d, 2H), 3.50–3.60 (m, 6H), 3.78 (m, 1H), 5.02 (dd, 2H), 5.75 (m, 1H), 6.50 (s, 1H), 7.09 (m, 6H), 7.28 (m, 15H). LRMS: m/z (ES$^+$) 655. [MH$^+$]. [α]$_D$=−0.64 (c=0.156, methanol).

Preparation 25

(−)-Methyl (2S)-2-((3S)-3-{[(benzyloxy)carbonyl]amino}pyrrolidinyl)-3-(1-propyl-1H-imidazol-4-yl)propanoate

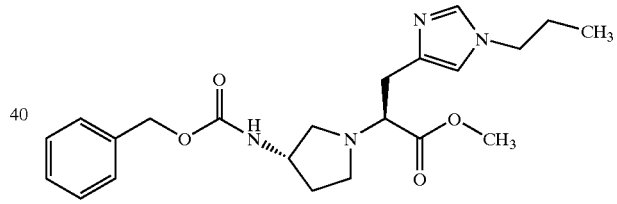

A solution of methanesulfonyl chloride (93 μl, 1.2 mmol) in dichloromethane (3 ml) was added dropwise to an ice-cooled solution of the alcohol from Preparation 20 (520 mg, 1.2 mmol) and triethylamine (340 μl, 2.4 mmol) in dichloromethane (30 ml), and the mixture was stirred at room temperature for 18 hours. The solution was evaporated under reduced pressure, the residue was partitioned between sodium bicarbonate solution and ethyl acetate and the phases were separated. The aqueous layer was extracted with ethyl acetate (3×20 ml) and the combined organic solutions were dried (Na$_2$SO$_4$) and evaporated under reduced pressure. The residual oil was purified by column chromatography on silica gel using an elution gradient of dichloromethane:methanol (100:0 to 95:5) to afford the title compound as a colourless oil, 354 mg. $^1$H-NMR (CDCl$_3$, 400 MHz) δ: 0.88 (t, 3H), 1.73 (m, 3H), 2.17 (m, 1H), 2.62 (m, 1H), 2.78 (m, 1H), 2.92 (m, 4H), 3.62 (m, 4H), 3.78 (t, 2H), 4.20 (m, 1H), 5.10 (s, 2H), 5.60 (m, 1H), 6.63 (s, 1H), 7.34 (m, 6H). LRMS: m/z (ES$^+$) 415 [MH$^+$]. [α]$_D$=−5.10 (c=0.117, dichloromethane).

Preparation 26

(−)-Methyl (2S)-2-((3S)-3-{[(benzyloxy)carbonyl]amino}pyrrolidinyl)-3-(1-isopentyl-1H-imidazol-4-yl)propanoate

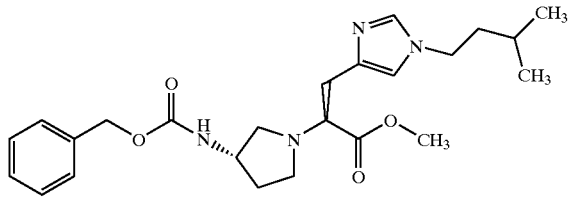

The title compound was obtained as a colourless oil in 74% yield from the alcohol from Preparation 21, following a similar procedure to that described in Preparation 25. ¹H-NMR (CDCl₃, 400 MHz) δ: 0.88 (d, 6H), 1.45 (m, 1H), 1.58 (m, 2H), 1.61 (m, 1H), 2.12 (m, 1H), 2.60 (dd, 1H), 2.75 (m, 1H), 2.81–2.97 (m, 4H), 3.60 (m, 4H), 3.79 (t, 2H), 4.18 (m, 1H), 5.05 (s, 2H), 5.61 (m, 1H), 6.60 (s, 1H), 7.22–7.35 (m, 6H). LRMS: m/z (ES⁺) 443 [MH⁺]. [α]$_D$=−1.15 (c=0.122, methanol).

Preparation 27

Methyl (2s)-2-((3S)-3-{[(benzyloxy)carbonyl]amino}pyrrolidinyl)-3-[1-(2-cyclohexylethy)-1H-imidazol-4-yl]propanoate

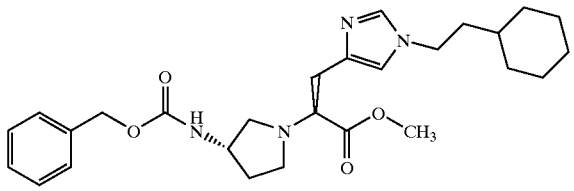

The title compound was obtained as a colourless oil in 97% yield from the alcohol from Preparation 22, following a similar procedure to that described in Preparation 25. ¹H-NMR (CD₃OD, 300 MHz) δ: 0.99 (m, 2H), 1.20 (m, 4H), 1.69 (m, 8H), 2.19 (m, 1H), 2.60 (m, 1H), 2.68 (m, 1H), 2.83–3.02 (m, 4H), 3.58 (t, 1H), 3.60 (s, 3H), 3.98 (t, 2H), 4.15 (m, 1H), 5.10 (s, 2H), 6.88 (s, 1H), 7.35 (m, 5H), 7.55 (s, 1H). LRMS: m/z (TSP⁺) 483.4 [MH⁺]. [α]$_D$=0.00 (c=0.104, methanol).

Preparation 28

(+)-Methyl (2S)-2-((3S)-3-{[(benzyloxy)carbonyl]amino}pyrrolidinyl)-3-[1-(2-phenylethyl)-1H-imidazol-4-yl]propanoate

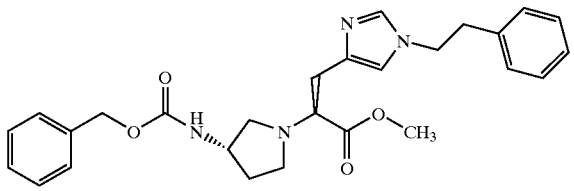

The title compound was obtained as a colourless oil in 91% yield from the alcohol from Preparation 23, following a similar procedure to that described in Preparation 25. ¹H-NMR (CDCl₃, 400 MHz) δ: 1.66 (m, 1H), 2.15 (m, 1H), 2.61 (m, 1H), 2.78 (m, 1H), 2.82–3.00 (m, 6H), 3.83 (m, 4H), 4.02 (t, 2H), 4.20 (m, 1H), 5.06 (s, 2H), 5.62 (m, 1H), 6.60 (s, 1H), 7.00 (m, 2H), 7.16 (s, 1H), 7.20–7.38 (m, 8H). LRMS: m/z (ES⁻) 475 [M−H⁻]. [α]$_D$=+3.84 (c=0.083, methanol).

Preparation 29

(−)-Methyl (2S)-2-((3S)-3-{[(benzyloxy)carbonyl]amino}pyrrolidinyl)-3-(1-trityl-1H-imidazol-4-yl)propanoate

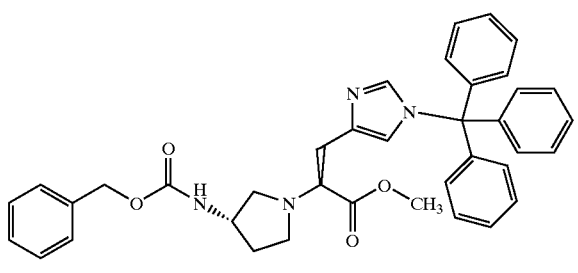

The title compound was obtained as a foam after evaporation from diethyl ether in 91% yield from the alcohol from Preparation 24, following a similar procedure to that described in Preparation 25. ¹H-NMR (CDCl₃, 400 MHz) δ: 1.59 (m, 1H), 2.09 (m, 1H), 2.57 (m, 1H), 2.64 (m, 1H), 2.80–2.98 (m, 4H), 3.57 (s, 3H), 3.60 (m, 1H), 4.15 (m, 1H), 5.01 (s, 2H), 5.40 (m, 1H), 6.50 (s, 1H), 7.05 (m, 6H), 7.24 (m, 15H). LRMS: m/z (ES⁺) 615 [MH⁺]. [α]$_D$=−6.08 (c=0.129, methanol).

Preparation 30

(+)-Methyl (2S)-2-((3S)-3-{[(benzyloxy)carbonyl]amino}pyrrolidinyl)-3-(1H-imidazol-4-yl)propanoate

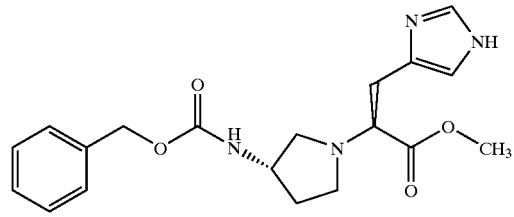

A solution of the imidazole from Preparation 29 (1 g, 1.63 mmol) in acetic acid (18 ml) and water (2 ml) was stirred at 60° C. for 1.5 hours. The solvent was evaporated under reduced pressure and the residue was suspended in water. The suspension was neutralised using sodium bicarbonate solution and extracted with dichloromethane (3×20 ml). The combined organic extracts were dried (Na₂SO₄) and evaporated under reduced pressure. The residual oil was purified by column chromatography on silica gel using an elution gradient of dichloromethane:methanol:0.88 ammonia (99.8:0:0.2 to 93.8:6:0.2) to give an oil. This was suspended in diethyl ether and the suspension was concentrated under reduced pressure to give a white solid, 458 mg. ¹H-NMR (CDCl₃, 400 MHz) δ: 1.74 (m, 1H), 2.19 (m, 1H), 2.68 (m, 1H), 2.80 (m, 1H), 2.97 (m, 3H), 3.07 (m, 1H), 3.62 (m, 1H), 3.64 (s, 3H), 4.20 (m, 1H), 5.09 (s, 1H), 5.22–5.40 (m, 1H), 6.80 (s, 1H), 7.35 (m, 5H), 7.50 (s, 1H). LRMS: m/z (ES⁻) 371 [M-H⁻]. [α]$_D$=+5.26 (c=0.129, methanol).

Preparation 31

(−)-Methyl (2S)-2-((3S)-3-{[(benzyloxy)carbonyl]amino}pyrrolidinyl)-3-[1-(3-cyclohexylpropyl)-1H-imidazol-4-yl]propanoate

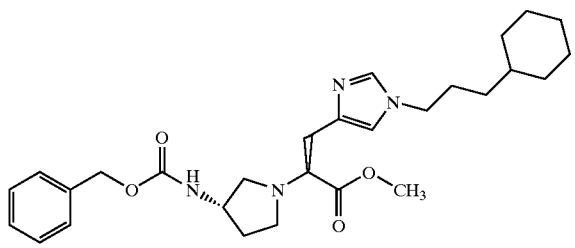

A mixture of the imidazole from Preparation 30 (750 mg, 2 mmol), 3-cyclohexylpropyl bromide (410 mg, 2 mmol) and cesium carbonate (660 mg, 2 mmol) in acetonitrile (40 ml) was heated at reflux for 18 hours. The cooled mixture was concentrated under reduced pressure and the residue was partitioned between ethyl acetate (20 ml) and sodium bicarbonate solution. The phases were separated, the aqueous layer was extracted with ethyl acetate (2×20 ml), and the combined organic solutions were dried (Na₂SO₄) and evaporated under reduced pressure to give an oil. This was purified in three sequential steps by column chromatography on silica gel, the first using an elution gradient of dichloromethane:methanol (100:0 to 96:4), the second using an elution gradient of toluene:diethylamine (100:0 to 97:3), and the third using an elution gradient of dichloromethane:methanol (100:0 to 97.5:2.5). The resulting oil was suspended in diethyl ether and the suspension was concentrated under reduced pressure to give the title compound as a colourless oil, 400 mg. ¹H-NMR (CDCl₃, 400 MHz) δ: 0.81 (m, 2H), 1.02–1.21 (m, 6H), 1.62 (m, 8H), 2.10 (m, 1H), 2.59 (m, 1H), 2.75 (m, 1H), 2.80–2.99 (m, 4H), 3.60 (m, 4H), 3.74 (m, 2H), 4.17 (m, 1H), 5.03 (s, 2H), 5.60 (m, 1H), 6.60 (s, 1H), 7.20–7.35 (m, 6H). LRMS: m/z (ES⁺) 519 [MNa⁺]. [α]$_D$=−4.07 (c=0.172, methanol).

Preparation 32

(−)-Methyl (2S)-2-((3S)-3-{[(benzyloxy)carbonyl]amino}pyrrolidinyl)-3-(1-phenyl-1H-imidazol-4-yl)propanoate

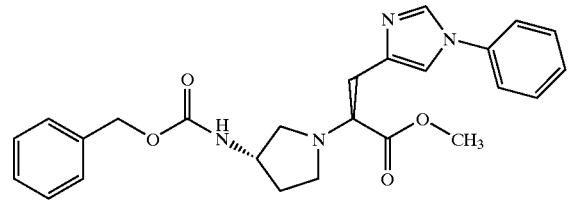

Compressed air was bubbled through a mixture of the imidazole from Preparation 30 (350 mg, 0.94 mmol), ben- zeneboronic acid (230 mg, 1.88 mmol), copper acetate (273 mg, 1.5 mmol), pyridine (0.15 ml, 1.88 mmol) and powdered 4 Å molecular sieves (40 mg) in dichloromethane (15 ml) for 6 hours at 22° C. The airflow was then stopped and the mixture was stirred for a further 18 hours at room temperature. The reaction mixture was diluted with a solution of ethylenediaminetetraacetic acid disodium salt (0.8 g) in water (20 ml), sodium bicarbonate solution (20 ml) and dichloromethane (50 ml), and the mixture was stirred vigorously for 2 hours. The layers were separated, the aqueous phase was extracted with dichloromethane (2×40 ml), and the combined organic solutions were washed with brine (3×40 ml), dried (Na₂SO₄) and evaporated under reduced pressure. The residual oil was purified by column chromatography on silica gel twice using an elution gradient of dichloromethane:methanol (100:0 to 96:4). The product was suspended in diethyl ether and the suspension was concentrated under reduced pressure to afford the title compound as a colourless oil, 100 mg. ¹H-NMR (CDCl₃ 400 MHz) δ:1.64 (m, 1H), 2.15 (m, 1H), 2.62 (m, 1H), 2.74–3.10 (m, 5H), 3.62 (s, 3H), 3.70 (m, 1H), 4.18 (m, 1H), 5.02 (m, 2H), 5.63 (m, 1H), 7.01 (s, 1H), 7.30 (m, 8H), 7.40 (m, 2H), 7.68 (m, 1H). LRMS: m/z (ES⁺) 471 [MNa⁺]. [α]$_D$=−7.80 (c=0.10, methanol).

Preparation 33

(−)-Dimethyl (2S)-2-[(tert-butoxycarbonyl)amino]butanedioate

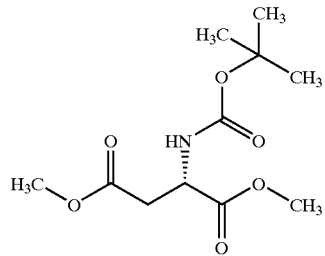

A solution of di-tert-butyl dicarbonate (10.3 g, 47 mmol) in dichloromethane (20 ml) was added dropwise to an ice-cooled solution of L-aspartic acid dimethyl ester hydrochloride (9.3 g, 47 mmol) and triethylamine (14.4 ml, 103 mmol) in dichloromethane (60 ml), and the mixture was stirred at room temperature for 18 hours. The solution was diluted with dichloromethane (60 ml), washed sequentially with water (5 ml), 5% aqueous sodium bicarbonate solution (50 ml) and brine (50 ml), then dried (Na₂SO₄) and evaporated under reduced pressure. The residual oil was triturated with hexane to afford the title compound as a white solid, 11 g. ¹H-NMR (CDCl₃ 300 MHz) δ: 1.45 (s, 9H), 2.81 (dd, 1H), 3.00 (dd, 1H), 3.70 (s, 3H), 3.77 (s, 3H), 4.59 (m, 1H), 5.50 (m, 1H). LRMS: m/z (ES⁺) 262 [MH⁺]. [α]$_D$=−10.91 (c=0.132, ethanol).

Preparation 34

(+)-Dimethyl (2R)-2-[(tert-butoxycarbonyl)amino]butanedioate

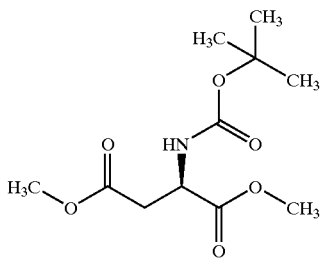

The title compound was obtained as a white solid in 94% yield, from D-aspartic acid dimethyl ester hydrochloride and di-tert-butyl dicarbonate, following the procedure described in Preparation 33. $^1$H-NMR (CDCl$_3$ 400 MHz) δ: 1.42 (s, 9H), 2.81 (dd, 1H), 3.00 (dd, 1H), 3.70 (s, 3H), 3.75 (s, 3H), 4.58 (m, 1H), 5.48 (m, 1H). LRMS: m/z (ES$^+$) 284 [MNa$^+$]. [α]$_D$=+18.1 (c=0.199, methanol).

Preparation 35

Dimethyl (2S)-2-[(tert-butoxycarbonyl)amino]pentanedioate

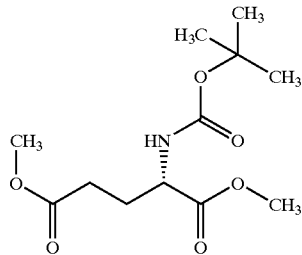

The title compound was obtained as an oil in 94% yield from L-glutamic acid dimethyl ester and di-tert-butyl dicarbonate, following a similar procedure to that described in Preparation 33. $^1$H-NMR (CDCl$_3$ 400 MHz) δ: 1.42 (s, 9H), 1.98 (m, 1H), 2.18 (m, 1H), 2.40 (m, 2H), 3.68 (s, 3H), 3.77 (s, 3H), 4.36 (m, 1H), 5.10 (m, 1H). LRMS m/z (ES$^+$) 298 [MNa$^+$].

Preparation 36

(−)-tert-Butyl (1S)-3-hydroxy-1-(hydroxymethyl)propylcarbamate

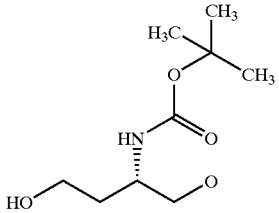

Sodium borohydride (880 mg, 23.0 mmol) was added to a solution of the ester from Preparation 33 (3.0 g, 11.5 mmol) in tetrahydrofuran (15 ml), and the mixture was warmed to 45° C. Dry methanol (1 ml) was added, the mixture was stirred for 20 minutes, further methanol (2 ml) was added dropwise so as to maintain a temperature of 50–55° C., and once addition was complete, the reaction was stirred at 50° C. for 1 hour then at room temperature for 18 hours. The mixture was cooled, diluted with 5% aqueous sodium bicarbonate solution (10 ml) and water (20 ml) and then extracted with ethyl acetate (3×30 ml). The combined organic extracts were washed with brine (3×20 ml), dried (Na$_2$SO$_4$) and evaporated under reduced pressure and the residue was triturated with hexane to afford the title compound as a white solid, 1.25 g. $^1$H-NMR (CDCl$_3$ 400 MHz) δ: 1.42 (s, 9H), 1.61 (m, 1H), 1.80 (m, 1H), 2.52 (m, 1H), 3.21 (m, 1H), 3.66 (m, 4H), 3.85 (m, 1H), 5.04 (m, 1H). LRMS: m/z (ES$^+$) 206 [MH$^+$]. [α]$_D$=−29.46 (c=0.126, ethanol).

Preparation 37

(+)-tert-Butyl (1R)-3-hydroxy-1-(hydroxymethyl)propylcarbamate

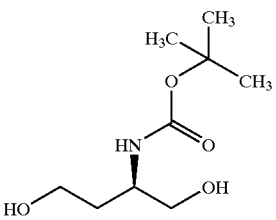

The title compound was obtained as a white solid in 59% yield from the ester from Preparation 34, following the procedure described in Preparation 36. $^1$H-NMR (CDCl$_3$ 300 MHz) δ: 1.42 (s, 9H), 1.61 (m, 1H), 1.80 (m, 1H), 2.38 (m, 1H), 3.08 (m, 1H), 3.06–3.94 (m, 5H), 5.00 (m, 1H). LRMS: m/z (ES$^+$) 228 [MNa$^+$]. [α]$_D$=+31.50 (c=0.126, ethanol).

Preparation 38

(−)-tert-Butyl (1S)-4-hydroxy-1-(hydroxymethyl)butylcarbamate

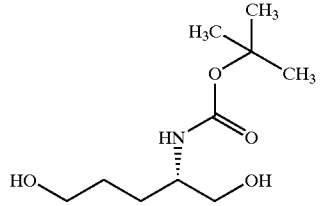

The title compound was obtained as colourless crystals in 78% yield from the ester from Preparation 35, following the procedure described in Preparation 36. $^1$H-NMR (CDCl$_3$ 300 MHz) δ: 1.42 (s, 9H), 1.49–1.59 (m, 4H), 1.80 (m, 1H), 2.40 (m, 1H), 3.55–3.74 (m, 5H), 4.78 (m, 1H). LRMS: m/z (ES$^+$) 242 [MNa$^+$]. [α]$_D$=−14.68 (c=0.154, dichloromethane).

Preparation 39

(−)-(2S)-2-[(tert-Butoxycarbonyl)amino]-4-[(methylsulfonyl)oxy]butyl methanesulfonate

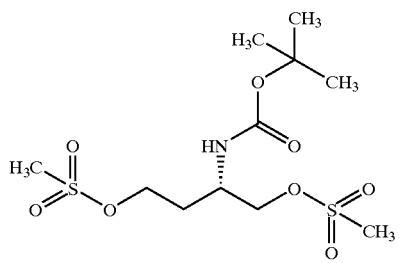

Triethylamine (1.63 ml, 12 mmol) was added to a cooled (−10° C.) suspension of the diol from Preparation 36 (1 g, 4.87 mmol) in ethyl acetate (15 ml). A solution of methanesulfonyl chloride (0.83 ml, 10 mmol) was added dropwise, and once addition was complete, the reaction was stirred for a further 2 hours. The mixture was diluted with ethyl acetate (30 ml), washed with water (2×30 ml), dried ($Na_2SO_4$) and evaporated under reduced pressure. The residue was triturated with hexane to afford the title compound as a white solid, 1.6 g. $^1$H-NMR (CDCl$_3$ 300 MHz) δ: 1.42 (s, 9H), 1.95–2.09 (m, 2H), 3.02 (s, 6H), 4.04 (m, 1H), 4.30 (m, 4H), 4.77 (m, 1H). LRMS: m/z (TSP$^+$) 379.1 [MNH$_4^+$]. [α]$_D$=−24.95 (c=0.135, acetone).

Preparation 40

(+)-(2R)-2-[(tert-Butoxycarbonyl)amino]-4-[(methylsulfonyl)oxy]butyl methanesulfonate

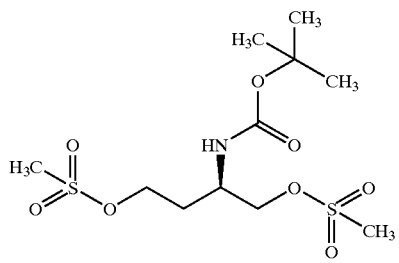

The title compound was obtained as a white solid in 91% yield, from the diol from Preparation 37, following the procedure described in. Preparation 39. $^1$H-NMR (CDCl$_3$ 300 MHz) δ: 1.42 (s, 9H), 1.95–2.10 (m, 2H), 3.04 (s, 6H), 4.05 (m, 1H), 4.30 (m, 4H), 4.79 (m, 1H). LRMS: m/z (TSP$^+$) 362.0 [MH$^+$]. [α]$_D$=+26.5 (c=0.1.19, acetone).

Preparation 41

(−)-(2S)-2-[(tert-Butoxycarbonyl)amino]-5-[(methylsulfonyl)oxy]pentyl methanesulfonate

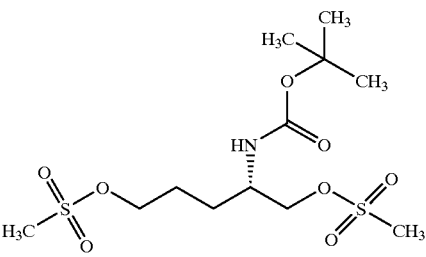

The title compound was obtained as a white solid in 85% yield, from the diol from Preparation 38, following a similar procedure to that described in Preparation 39. $^1$H-NMR (CDCl$_3$ 300 MHz) δ: 1.42 (s, 9H), 1.58–1.94 (m, 4H), 3.02 (2xs, 6H), 3.92 (m, 1H), 4.22 (m, 4H), 4.64 (m, 1H). LRMS: m/z (ES$^+$) 398.0 [MNa$^+$]. [α]$_D$=−17.87 (c=0.122, dichloromethane).

Preparation 42

(+)-Methyl (2S)-2-{(3S)-3-[(tert-butoxycarbonyl)amino]pyrrolidinyl}-3-(1-trityl-1H-imidazol-4-yl)propanoate

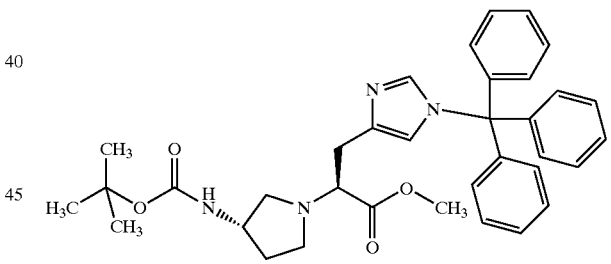

The mesylate from Preparation 39 (900 mg, 2.5 mmol) was added to a solution of methyl (2S)-2-amino-3-(1-trityl-1H-imidazol-4-yl)propanoate (4.0 g, 10 mmol) in dichloromethane (30 ml) and the mixture was heated under reflux for 6 days. The cooled mixture was washed with sodium bicarbonate solution (30 ml) and brine (3×20 ml), then dried ($Na_2SO_4$) and concentrated under reduced pressure. The residual oil was purified twice by column chromatography on silica gel using an elution gradient of dichloromethane:methanol (100:0 to 96:4) to afford the title compound as a colourless foam, 180 mg. $^1$H-NMR (CDCl$_3$ 300 MHz) δ: 1.40 (s, 9H), 1.62 (m, 1H), 2.14 (m, 1H), 2.55–2.70 (m, 2H), 2.84 (m, 2H), 2.97 (d, 2H), 3.59 (m, 4H), 4.10 (m, 1H), 5.20 (m, 1H), 6.58 (s, 1H), 7.12 (m, 6H), 7.36 (m, 10H). LRMS: m/z (ES$^+$) 581 [MH$^+$]. [α]$_D$=+13.23 (c=0.039, dichloromethane).

Preparation 43

(−)-Methyl (2R)-2-{(3S)-3-[(tert-butoxycarbonyl)amino]pyrrolidinyl}-3-(1-trityl-1H-imidazol-4-yl)propanoate

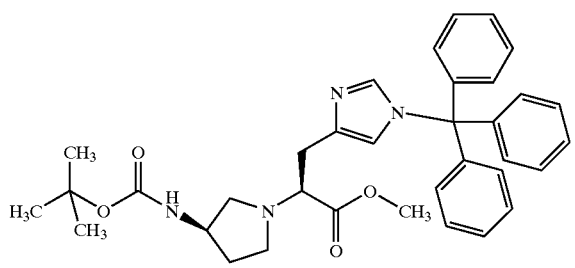

The title compound was obtained as a colourless foam in 16% yield from the mesylate from Preparation 40 and methyl (2S)-2-amino-3-(1-trityl-1H-imidazol-4-yl)propanoate following a similar procedure to that described in Preparation 42. $^1$H-NMR (CDCl$_3$ 300 MHz) δ: 1.41 (s, 9H), 1.62 (m, 1H), 2.00–2.19 (m, 1H), 2.62 (m, 2H), 2.82 (m, 2H), 2.98 (t, 2H), 3.58 (s, 3H), 3.62 (m, 1H), 4.10 (m, 1H), 4.97 (m, 1H), 6.56 (s, 1H), 7.10 (m, 6H), 7.32 (m, 10H). LRMS: m/z (ES$^+$) 582 [MH$^+$]. [α]$_D$=−10.40 (c=0.125, dichloromethane).

Preparation 44

(−)-Methyl (2S)-2-{(3S)-3-[(tert-butoxycarbonyl)amino]-1-piperidinyl}-3-(1-trityl-1H-imidazol-4-yl)propanoate

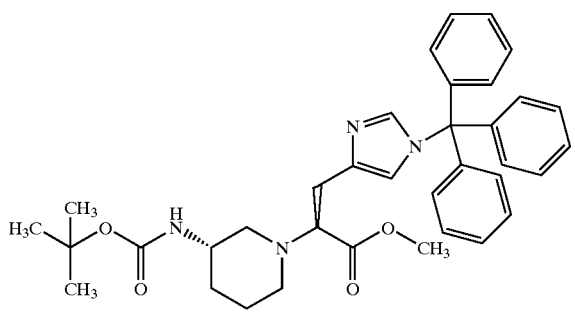

The title compound was obtained as a colourless foam in 8% yield from the mesylate from Preparation 41 and methyl (2S)-2-amino-3-(1-trityl-1H-imidazol-4-yl)propanoate following a similar procedure to that described in Preparation 42. $^1$H-NMR (CDCl$_3$ 300 MHz) δ: 1.30–1.44 (m, 1.1H), 1.64 (m, 2H), 2.58 (m, 3H), 2.80 (m, 1H), 2.88 (d, 2H), 3.45 (m, 1H), 3.60 (s, 3H), 3.67 (m, 1H), 6.14 (bs, 1H), 6.58 (s, 1H), 7.14 (m, 6H), 7.30 (m, 9H), 7.38 (s, 1H). LRMS: m/z (ES$^+$) 595 [MH$^+$]. [α]$_D$=−25.34 (c=0.075, dichloromethane).

Preparation 45

Methyl (2S)-2-{(3S)-3-[(tert-butoxycarbonyl)amino]pyrrolidinyl}-3-(1H-imidazol-4-yl)propanoate

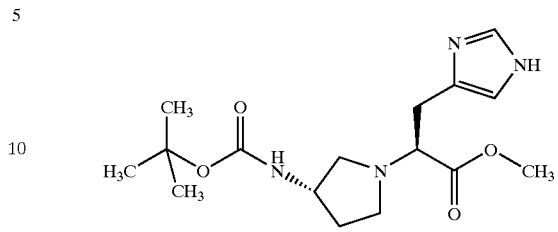

A mixture of the protected imidazole from Preparation 42 (230 mg, 0.40 mmol) and 90% acetic acid (10 ml) was stirred at 60° C. for 90 minutes. The cooled solution was concentrated under reduced pressure, the residue was dissolved in water and the resulting solution was basified using sodium bicarbonate solution. This aqueous mixture was extracted with dichloromethane (3×20 ml) and the combined organic extracts were washed with brine (3×20 ml), dried (Na$_2$SO$_4$) and evaporated under reduced pressure. The residual oil was purified by column chromatography on silica gel using an elution gradient of dichloromethane:methanol (100:0 to 92:8) to afford the title compound as an oil, 98 mg. $^1$H-NMR (CDCl$_3$ 300 MHz) δ: 1.43 (s, 9H), 1.68 (m, 1H), 2.18 (m, 1H), 2.74 (m, 2H), 2.90–3.14 (m, 4H), 3.60 (t, 1H), 3.66 (s, 3H), 4.15 (m, 1H), 5.00 (bs, 1H), 6.81 (s, 1H), 7.56 (s, 1H). LRSM: m/z (ES$^+$) 339 [MH$^+$].

Preparation 46

Methyl (2S)-2-{(3S)-3-[(tert-butoxycarbonyl)amino]pyrrolidinyl}-3-(1-propyl-1H-imidazol-4-yl)propanoate

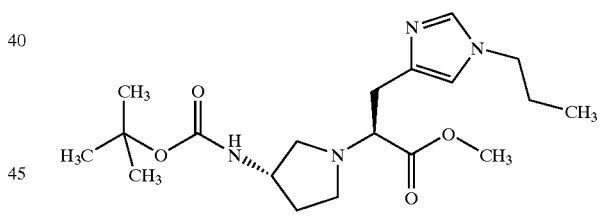

n-Propyl bromide (25 μl, 0.28 mmol) was added to a suspension of the imidazole from Preparation 45 (95 mg, 0.28 mmol) and potassium carbonate (60 mg, 0.56 mmol) in acetonitrile (20 ml) and the reaction mixture was heated under reflux for 18 hours. TLC analysis showed starting material remaining, so additional n-propyl bromide (25 μl, 0.28 mmol) and potassium carbonate (30 mg, 0.28 mmol) were added and the mixture was heated under reflux for a further 18 hours. TLC analysis showed starting material remaining, so additional n-propyl bromide (25 μl, 0.28 mmol) was added and the mixture was heated under reflux for a further 18 hours. The cooled mixture was concentrated under reduced pressure, the residue was dissolved in water and the resulting solution was extracted with dichloromethane (3×20 ml). The combined organic extracts were dried (Na$_2$SO$_4$) and evaporated under reduced pressure. The residual oil was purified by column chromatography on silica gel using an elution gradient of dichloromethane:methanol (100:0 to 92:8) to afford the title compound as an oil, 18 mg. ¹H-NMR (CDCl₃ 300 MHz) δ: 1.42 (s, 9H), 1.62 (m, 1H), 1.78 (m, 5H), 2.16 (m, 1H), 2.57–2.72 (m, 2H), 2.84–3.00 (m, 4H), 3.62 (s, 4H), 3.80 (t, 2H), 4.15 (m, 1H), 5.15 (bs, 1H), 6.64 (s, 1H), 7.36 (s, 1H). LRMS: m/z (ES⁺) 381 [MH⁺].

Preparation 47

Methyl 2-[(3S)-3-aminopyrrolidinyl]-3-(1H-imidazol-4-yl)propanoate bis(trifluoroacetate)

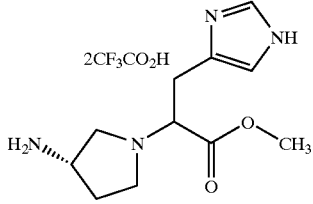

Trifluoroacetic acid (4 ml) was added to a solution of the protected amino acid from Preparation 2 (175 mg, 0.52 mmol) in dichloromethane (4 ml), and the mixture was stirred at room temperature for 18 hours. The solution was concentrated under reduced pressure and the residue was azeotroped with dichloromethane (3×20 ml) then with diethyl ether (3×20 ml) to afford the title compound as an orange oil, 400 mg. ¹H-NMR (D₂O, 300 MHz) (mixture of diastereoisomers) δ: 2.06–2.25 (m, 1H), 2.46–3.64 (m, 1H), 3.37–3.78 (m, 8H), 3.80–4.00 (m, 1H), 4.14 (m, 1H), 4.29 (m, 1H), 7.38 (s, 1H), 8.60 (s, 1H). LRMS: m/z (ES⁺) 239.1 [MH⁺].

Preparation 48

2-{(3S)-3-[(tert-Butoxycarbonyl)amino]pyrrolidinyl}-3-(1H-imidazol-4-yl)propanoic Acid

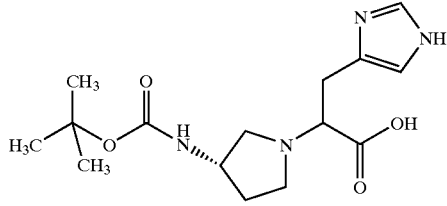

Sodium hydroxide solution (3 ml, 2M) was added to a solution of the ester from Preparation 2 (320 mg, 0.95 mmol) in dioxan (10 ml), and the mixture was stirred at room temperature for 18 hours. The solution was concentrated under reduced pressure, diluted with water, and purified by column chromatography on Dowex® 50WX8 ion-exchange resin, using an elution gradient of water:0.88 ammonia (100:0 to 95:5) to afford the title compound, 160 mg. ¹H-NMR (D₂O, 300 MHz) (mixture of diastereoisomers) δ: 1.32 (s, 9H), 1.78–1.97 (m, 1H), 2.20–2.38 (m, 1H), 3.00–3.58 (m, 6H), 3.68 (m, 1H), 4.18 (m, 1H), 6.92 (s, 1H), 7.64 (s, 1H). LRMS: m/z (ES⁺) 347 [MNa⁺]. HRMS: 325.1877 [MH⁺] C₁₅H₂₄N₄O₄ requires 324.38.

Preparation 49

(+)-(2S)-2-((3S)-3-{[(Benzyloxy)carbonyl]amino}pyrrolidinyl)-3-(1-propyl-1H-imidazol-4-yl)propanoic Acid

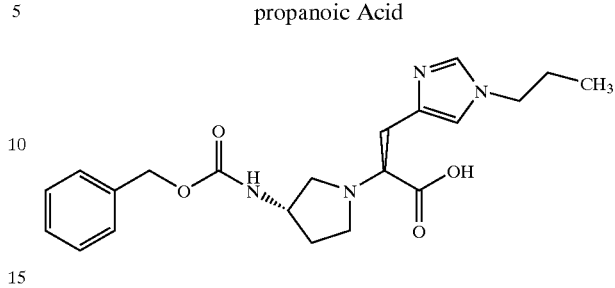

Sodium hydroxide solution (0.72 ml, 5M) was added to a solution of the ester from Preparation 25 (300 mg, 0.72 mmol) in dioxan (14 ml), and the mixture was stirred at room temperature for 72 hours. The solution was concentrated under reduced pressure, diluted with water, and purified by column chromatography on Dowex® 50WX8 ion-exchange resin, using an elution gradient of water:0.88 ammonia (100:0 to 95:5) to give a solid. This was purified by column chromatography on silica gel using an elution gradient of dichloromethane:methanol:0.88 ammonia (95:5:0.5 to 90:10:0.5) to afford the title compound as a colourless foam, 140 mg. ¹H-NMR (CD₃OD, 300 MHz) δ: 0.88 (t, 3H), 1.78 (m, 2H), 1.90 (m, 1H), 2.35 (m, 1H), 3.14 (d, 2H), 3.20–3.50 (m, 4H), 3.62 (m, 1H), 3.90 (t, 2H), 4.22 (m, 1H), 5.07 (s, 2H), 6.98 (s, 1H), 7.34 (m, 5H), 7.58 (s, 1H). LRMS: m/z (ES⁺) 401 [MH⁺]. [α]$_D$=+16.4 (c=0.238, methanol).

Preparation 50

(+)-(2)-2-((3S)-3-{[(Benzyloxy)carbonyl]amino}pyrrolidinyl)-3-(1-isopentyl-1H-imidazol-4-yl)propanoic Acid

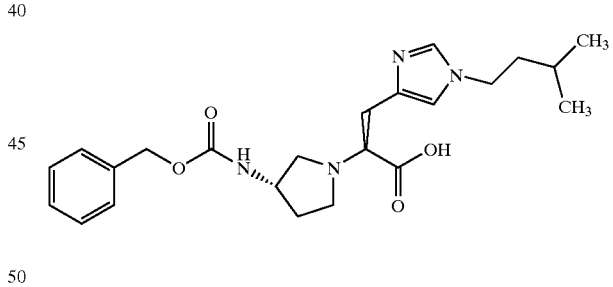

Sodium hydroxide solution (0.4 ml, 5M) was added to a solution of the ester from Preparation 26 (175 mg, 0.40 mmol) in dioxan (12 ml) and water (6 ml), and the mixture was stirred at room temperature for 18 hours. The solution was concentrated under reduced pressure, diluted with water, and purified by column chromatography on Dowex® 50WX8 ion-exchange resin, using an elution gradient of water:0.88 ammonia:methanol (100:0:0 to 90:5:5) to give a foam. This was suspended in ethyl acetate/methanol, the suspension was filtered and the filtrate was concentrated under reduced pressure and azeotroped with ether to afford the title compound as a colourless solid, 100 mg. ¹H-NMR (CD₃OD, 300 MHz) δ: 0.96 (d, 6H), 1.56 (m, 1H), 1.64 (m, 2H), 1.98 (m, 1H), 2.38 (m, 1H), 3.19 (d, 2H), 3.40 (m, 1H), 3.49–3.63 (m, 3H), 3.81 (t, 1H), 3.98 (t, 2H), 4.27 (m, 1H), 5.08 (s, 2H), 7.00 (s, 1H), 7.32 (m, 5H), 7.59 (s, 1H). LRMS: m/z (ES⁻) 427 [M–H⁻]. [α]$_D$=+14.03 (c=0.083, methanol).

Preparation 51

(+)-(2S)-2-{(3S)-3-[(Benzyloxycarbonyl)amino]
pyrrolidinyl}-3-[1-(2-cyclohexylethyl)-1H-imidazol-
4-yl]propanoic Acid

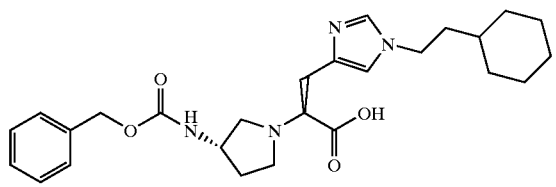

The title compound was obtained as a colourless foam in 78% yield from the ester from Preparation 27, following the procedure described in Preparation 50. $^1$H-NMR (CD$_3$OD, 400 MHz) δ: 0.95 (m, 2H), 1.18 (m, 4H), 1.60–1.74 (m, 7H), 1.92 (m, 1H), 2.34 (m, 1H), 3.14 (d, 2H), 3.35 (m, 1H), 3.40–3.60 (m, 4H), 3.76 (t, 1H), 3.94 (t, 2H), 4.22 (m, 1H), 5.04 (s, 2H), 6.98 (s, 1H), 7.27 (m, 5H), 7.57 (s, 1H). [α]$_D$=+14.69 (c=0.112, methanol).

Preparation 52

(+)-(2S)-2-{(3S)-3-[(Benzyloxycarbonyl)amino]
pyrrolidinyl}-3-[1-(3-cyclohexylpropyl)-1H-
imidazol-4-yl]propanoic Acid

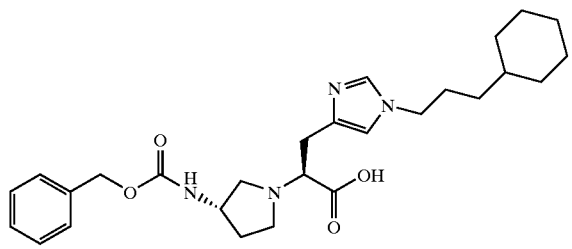

The title compound was obtained as a colourless foam in 54% yield from the ester from Preparation 31, following a similar procedure to that described in Preparation 50. $^1$H-NMR (CD$_3$OD, 400 MHz) δ: 0.86 (m, 2H), 1.12–1.30 (m, 6H), 1.60–1.93 (m, 8H), 2.28 (m, 1H), 3.10 (m, 2H), 3.18 (m, 2H), 3.38 (m, 2H), 3.60 (m, 1H), 3.90 (t, 2H), 4.20 (m, 1H), 5.06 (s, 2H), 6.98 (s, 1H), 7.30 (m, 5H), 7.53 (s, 1H). LRMS: m/z (ES$^+$) 483 [MH$^+$]. [α]$_D$=+9.8 (c=0.215, methanol).

Preparation 53

(2S)-2-{(3S)-3-[(Benzyloxycarbonyl)amino]
pyrrolidinyl}-3-[1-(2-phenylethyl)-1H-imidazol-4-
yl]propanoic Acid

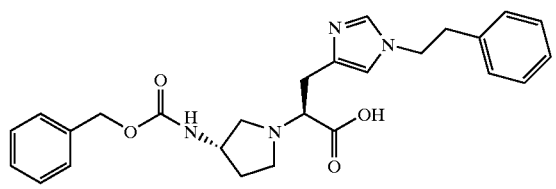

The title compound was obtained as a colourless foam in 58% yield from the ester from Preparation 28, following a similar procedure to that described in Preparation 50. $^1$H-NMR (CD$_3$OD, 400 MHz) δ: 1.94 (m, 1H), 2.32 (m, 1H), 3.00 (t, 2H), 3.12 (d, 2H), 3.36–3.60 (m, 4H), 3.78 (m, 1H), 4.18 (t, 2H), 4.22 (m, 1H), 5.03 (s, 2H), 6.95 (s, 1H), 7.05 (m, 2H), 7.15 (m, 1H), 7.20–7.34 (m, 8H). LRMS: m/z (ES$^-$) 461 [M–H$^-$]. [α]$_D$=+17.72 (c=0.114, methanol).

Preparation 54

(2S)-2-{(3S)-3-[(Benzyloxycarbonyl)amino]
pyrrolidinyl}-3-[1-phenyl-1H-imidazol-4-yl]
propanoic Acid

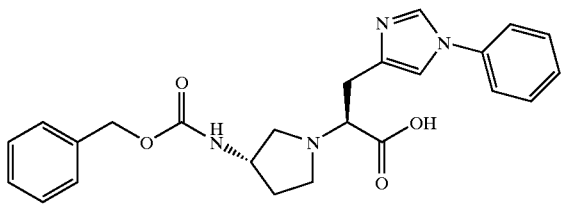

Sodium hydroxide solution (0.2 ml, 5M) was added to a solution of the ester from Preparation 32 (90 mg, 0.20 mmol) in dioxan (5 ml) and water (2 ml), and the mixture was stirred at room temperature for 18 hours. The solution was concentrated under reduced pressure, diluted with water, and purified by column chromatography on Dowex® 50WX8 ion-exchange resin, using an elution gradient of water:0.88 ammonia (100:0 to 90:5) to give the title compound as a foam, 60 mg. $^1$H-NMR (CD$_3$OD, 400 MHz) δ: 2.00 (m, 1H), 2.40 (m, 2H), 3.41–3.80 (m, 5H), 3.86 (m, 1H), 4.30 (m, 1H), 5.08 (m, 2H), 7.25–7.40 (m, 5H), 7.42 (s, 1H), 7.52 (m, 5H), 7.98–8.08 (m, 1H). LRMS: m/z (ES$^+$) 457 [MNa$^+$].

Preparation 55

Sodium (2S)-2-{(3S)-3-[(tert-butoxycarbonyl)
amino]pyrrolidinyl}-3-(1-trityl-1H-imidazol-4-yl)
propanoate

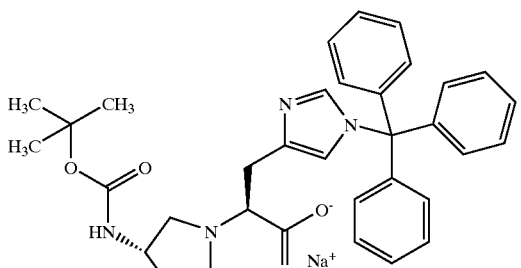

Sodium hydroxide solution (0.22 ml, 5M) was added to a solution of the ester from Preparation 42 (130 mg, 0.22 mmol) in dioxan (5 ml) and the mixture was stirred at room temperature for 18 hours. Water (5 ml) was added, the mixture stirred for a further 2 hours, and evaporated under reduced pressure to give a paste, which was used without further purification. $^1$H-NMR (D$_2$O, 300 MHz) δ: 1.28 (s, 9H), 1.44 (m, 1H), 2.00 (m, 1H), 2.17 (m, 1H), 2.58 (m, 2H), 2.72 (m, 2H), 2.90 (m, 1H), 3.10 (m, 1H), 3.88 (m, 1H), 6.67 (s, 1H), 7.08 (m, 6H), 7.20 (m, 9H), 7.42 (s, 1H). LRMS: m/z (ES$^+$) 567 [MH$^+$].

Preparation 56

(2S)-2-{(3R)-3-[(tert-butoxycarbonyl)amino]pyrrolidinyl}-3-(1-trityl-1H-imidazol-4-yl)propanoic Acid

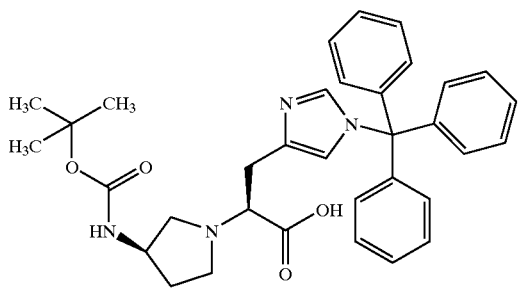

A mixture of the ester from Preparation 43 (300 mg, 0.52 mmol) and sodium hydroxide solution (0.51 ml, 5M) in dioxan (14 ml) and water (7 ml) was stirred at room temperature for 18 hours. The reaction mixture was concentrated under reduced pressure, the residue was diluted with water, and the resulting solution was acidified to pH 4 using hydrochloric acid. Sodium bicarbonate solution was added to adjust the pH to 6.5, and the mixture was extracted with ethyl acetate (3×20 ml). The combined organic extracts were dried ($Na_2SO_4$) and evaporated under reduced pressure. The residual oil was purified by column chromatography on silica gel using dichloromethane:methanol:0.88 ammonia (90:10:1) as eluant, to afford, after azeotroping with ether, the title compound as a white solid, 180 mg. $^1$H-NMR (DMSO-$d_6$, 300 MHz) δ: 1.37 (s, 9H), 1.52 (m, 1H), 1.90 (m, 1H), 2.62–2.82 (m, 5H), 2.95 (m, 1H), 3.83 (m, 1H), 6.60 (s, 1H), 7.02 (m, 6H), 7.20 (s, 1H), 7.38 (m, 10H). LRMS: m/z ($ES^+$) 568 [$MH^+$].

Preparation 57

Sodium (2S)-2-{(3S)-3-[(tert-butoxycarbonyl)amino]piperidinyl}-3-(1-trityl-1H-imidazol-4-yl)propanoate

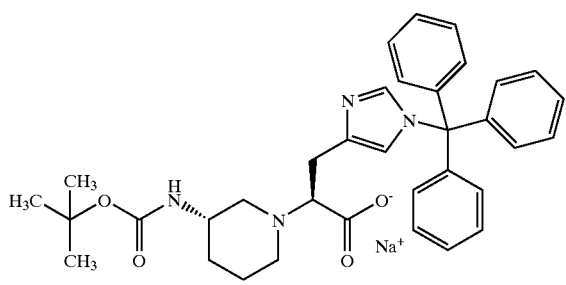

The title compound was obtained crude, from the ester from Preparation 44, following a similar procedure to that described in Preparation 55. LRMS: m/z ($ES^+$) 581 [$MH^+$]

The compounds of the present invention may be tested using the following assay, which is based on that disclosed in Boffa et al., *J. Biol. Chem.* 1998, 273, 2127. The compounds are incubated with activated TAFI and a standard substrate for TAFIa, the rate of hydrolysis of the substrate is determined and compared to the rate of hydrolysis in the absence of the compounds, and the amount of inhibition expressed in terms of $K_i$.

Assay for TAFIa Inhibition i) TAFI Activation

Human TAFI (recombinant or purified) was activated by incubating 20 μl of stock solution (360 μg/ml) with 10 μl of human thrombin (10 NIH units/ml), 10 μl of rabbit thrombomodulin (30 μg/ml), 6 μl calcium chloride (50 mM) in 50 μL of 20 mM HEPES (N-[2-hydroxyethyl]piperazine-N-[2-ethanesulfonic acid]) buffer containing 150 mM sodium chloride and 0.01% TWEEN 80 (polyoxyethylene-sorbitan monooleate) pH 7.6 for 20 minutes at 22° C. At the end of the incubation period, thrombin was neutralised by the addition of 10 μL of PPACK (D-Phe-Pro-Arg chloromethyl ketone) (100 nM). The resulting TAFIa solution was stored on ice for 5 minutes and finally diluted with 175 μl of HEPES buffer.

ii) $K_i$ Determination (TAFIa)

Calculated $K_i$

A number of different dilutions of the test compound in water were made up. To 20 μl of each dilution was added 150 μl of HEPES buffer and 10 μl of TAFIa, which was then pre-incubated for 15 minutes at 24° C. To each dilution was then added 20 μl furylacryloyl-alanyl-lysine (FAAL) at a standard concentration. Substrate turnover was measured by reading the absorbance of the reaction mixture at 330 nm every 15 seconds for 30 minutes. The reaction was performed at 24° C. and samples were mixed for 3 seconds prior to each absorbance reading.

A graph of % inhibition against test compound concentration was then plotted; from which was calculated the $IC_{50}$ value. The $K_i$ value was then calculated using the Cheng-Prusoff equation.

Two controls, positive and negative, were used to check the accuracy of the results in each case. For the first control, the assay was performed as above, but with 20 μl of water rather than a dilution of the test compound. This showed minimal inhibition. For the second control, the assay was performed as above, but with an effective amount of a non specific carboxypeptidase inhibitor rather than a dilution of the test compound. This showed maximal inhibition. When the two controls did not demonstrate minimal and maximal inhibition respectively then the results were discounted and the test compound was reanalysed.

Using the above assay the compounds of the Examples were found to be potent and selective inhibitors of TAFIa. All the compounds tested had a $K_i$ value less than 20 μM. The specific $K_i$ values of certain compounds are detailed below:

| Compound of Example: | $K_i$(TAFIa) |
| --- | --- |
| 2 | 60 nM |
| 4 | 22 nM |
| 6 | 7 nM |
| 8 | 10 nM |
| 9 | 8 nM |

The selectivity of the compounds of the present invention for TAFIa over CPN was determined by calculating the $K_i$ of the compounds of the present invention for CPN, then comparing it to the $K_i$ for TAFIa. The $K_i$ was calculated using the assay for the calculation of TAFIa $K_i$, but substituting 10 μl of human CPN for 10 μl of TAFIa. Those compounds of the present invention tested exhibited a strong selectivity for TAFIa over CPN of the order of >50:1. The specific $K_i$ values and calculated selectivities of certain compounds are detailed below:

| Compound of Example: | $K_i$(CPN) | Selectivity |
|---|---|---|
| 4 | >10 μM | >450 |
| 6 | >10 μM | >1400 |

What is claimed is:

1. A medicament according to formula (I)

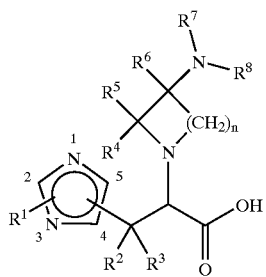

(I)

wherein:

n is 1, 2, 3 or 4;

$R^1$ is selected from
- (a) an optionally substituted straight chain or branched chain $C_{1-6}$ alkyl group,
- (b) an optionally substituted straight chain or branched chain $C_{2-6}$ alkenyl group,
- (c) an optionally substituted straight chain or branched chain $C_{2-6}$ alkynyl group,
- (d) Aryl,
- (e) Aromatic heterocycle,
- (f) Heterocycle, and
- (g) hydrogen;
- where the optional substituents in groups (a), (b) and (c) above are selected from: $C_{3-7}$ cycloalkyl, Aryl, Aromatic heterocycle, Heterocycle, $OR^9$, $NR^9R^{10}$, $S(O)_pR^9$, $OC(O)R^{10}$, $CO_2R^9$, $CONR^9R^{10}$, $SO_2NR^9R^{10}$, halo and $NHSO_2R^9$, and where p is 0, 1 or 2;

$R^2$, $R^3$, $R^4$, $R^5$, $R^6$, $R^7$ and $R^8$ are each independently selected from hydrogen and straight chain or branched chain $C_{1-6}$ alkyl optionally substituted by $OR^9$ or halo;

$R^9$ and $R^{10}$ are each independently selected from hydrogen and straight chain or branched chain $C_{1-6}$ alkyl;

Aryl is a 6–14 membered aromatic monocyclic or fused polycyclic carbocyclic group optionally substituted with one or more groups selected from $R^{11}$, halo, $OR^{12}$, $NR^{12}R^{13}$, $NR^{12}CO_2R^{11}$, $CO_2R^{12}$, $NR^{12}SO_2R^{11}$, CN, haloalkyl, O(haloalkyl), $SR^{12}$, $S(O)R^{11}$, $SO_2R^{11}$, $OC(O)R^{12}$, $SO_2NR^{12}R^{13}$ and $C(O)NR^{12}R^{13}$, where $R^{11}$ is straight chain or branched chain $C_{1-6}$ alkyl and $R^{12}$ and $R^{13}$ are each independently selected from hydrogen and straight chain or branched chain $C_{1-6}$ alkyl;

Aromatic heterocycle is a 5 to 7 membered aromatic ring containing from 1 to 3 heteroatoms, each independently selected from O, S and N, said ring being optionally substituted with one or more groups selected from $OR^{12}$, $NR^{12}R^{13}$, $CO_2R^{12}$, $NR^{12}CO_2R^{11}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{12}$, $NR^{12}R^{13}$, $CO_2R^{12}$, $NR^{12}CO_2R^{13}$, $R^{11}$, halo, CN, haloalkyl, O(haloalkyl), $SR^{12}$, $S(O)R^{11}$, $SO_2R^{11}$, $OC(O)R^{12}$, $NR^{12}SO_2R^{11}$, $SO_2NR^{12}R^{13}$ and $C(O)NR^{12}R^{13}$, or a tautomer thereof, or a pharmaceutically acceptable salt or solvate of said medicament or said tautomer wherein said medicament is for the treatment of a condition selected from thrombotic conditions, atherosclerosis, adhesions, dermal scarring, fibrotic conditions and inflammatory diseases.

* * * * *